(12) United States Patent
Blank et al.

(10) Patent No.: US 11,142,575 B2
(45) Date of Patent: Oct. 12, 2021

(54) METHODS FOR ENHANCING IMMUNOSUPPRESSIVE THERAPY BY MULTIPLE ADMINISTRATION OF αβTCR-BINDING POLYPEPTIDE

(71) Applicants: Genzyme Corporation, Cambridge, MA (US); EBERHARD KARLS UNIVERSITÄT TÜBINGEN, Tübingen (DE)

(72) Inventors: Gregor Blank, Tübingen (DE); Rupert Handgretinger, Tübingen (DE); Karin Schilbach, Tübingen (DE); Gina Lacorcia, Bridgewater, NJ (US); Daniel Snell, Thalwil (CH); Andreas Menrad, Oranienburg (DE)

(73) Assignees: GENZYME CORPORATION, Cambridge, MA (US); EBERHARD KARLS UNIVERSITÄT TÜBINGEN, Tübingen (DE)

(*) Notice: Subject to any disclaimer, the term of this patent is extended or adjusted under 35 U.S.C. 154(b) by 549 days.

(21) Appl. No.: 15/029,770

(22) PCT Filed: Oct. 30, 2014

(86) PCT No.: PCT/US2014/063254
§ 371 (c)(1),
(2) Date: Apr. 15, 2016

(87) PCT Pub. No.: WO2015/066379
PCT Pub. Date: May 7, 2015

(65) Prior Publication Data
US 2016/0244523 A1   Aug. 25, 2016

Related U.S. Application Data

(60) Provisional application No. 61/897,809, filed on Oct. 30, 2013.

(51) Int. Cl.
*C07K 16/28* (2006.01)
*A61K 39/00* (2006.01)

(52) U.S. Cl.
CPC .... *C07K 16/2809* (2013.01); *A61K 2039/505* (2013.01); *A61K 2039/545* (2013.01); *C07K 2317/24* (2013.01); *C07K 2317/54* (2013.01); *C07K 2317/55* (2013.01); *C07K 2317/56* (2013.01); *C07K 2317/565* (2013.01); *C07K 2317/567* (2013.01); *C07K 2317/73* (2013.01); *C07K 2317/75* (2013.01)

(58) Field of Classification Search
None
See application file for complete search history.

(56) References Cited

U.S. PATENT DOCUMENTS

| 2004/0002587 | A1 | 1/2004 | Watkins et al. |
| 2005/0058641 | A1 | 3/2005 | Siemionow |
| 2008/0038260 | A1 | 2/2008 | Ponath et al. |
| 2010/0190247 | A1 | 7/2010 | Lazar et al. |
| 2015/0099861 | A1 | 4/2015 | Snell et al. |

FOREIGN PATENT DOCUMENTS

| EP | 0 403 156 A1 | 12/1990 | |
| WO | 2006/105021 A2 | 10/2006 | |
| WO | 2008/086006 A2 | 7/2008 | |
| WO | 2010/027797 A1 | 3/2010 | |
| WO | 2011/109400 A2 | 9/2011 | |
| WO | WO-2012012737 A2 * | 1/2012 | ........... C12N 5/0637 |
| WO | 2013/037484 A2 | 3/2013 | |

OTHER PUBLICATIONS

Knight et al. (Transplantation. Jun. 15, 1994;57(11):1581-8) (Year: 1994).*
Ulivieri et al., Expert Review of Vaccines, 12:3, 297-310 (2013). (Year: 2013).*
Chen et al., Eur. J. Immunol. 1992. 22: 805-810. (Year: 1992).*
Koulmanda et al., Xenotransplantation 2004: 11: 525-530. (Year: 2004).*
Ashkenazi et al., PLoS ONE 8(5): e63625. (Year: 2002).*
Waid et al. (Drug Design, Development and Therapy 2009:3 205-212). (Year: 2009).*
Fuss et al., The Journal of Clinical Investigation, vol. 113 No. 10, 2004, p. 1490-1497. (Year: 2004).*
Yu et al., Inflamm Bowel Dis. Feb. 2007;13(2):191-9. (Year: 2007).*
Powrie et al., Ann. N.Y. Acad. Sci. 1029: 132-141 (2004), at p. 135-36. (Year: 2004).*
Getts et al., Immunotherapy (2011) 3(7), 853-870. (Year: 2011).*
Lavasani et al., Scand. J. Immunol. 65(1), 39-47 (2007). (Year: 2007).*

(Continued)

*Primary Examiner* — Zachary S Skelding
(74) *Attorney, Agent, or Firm* — Lathrop GPM LLP; James H. Velema, Esq.

(57) ABSTRACT

The present disclosure is related to improved methods for use of a humanized binding polypeptide specific for the alpha beta T cell receptor (αβ-TCR). In particular, this disclosure relates to improved methods of use of a humanized anti-αβ-TCR antibody, which is derived from the murine monoclonal antibody BMA031, in immunosuppressive therapy. Novel methods using humanized monoclonal antibodies and/or humanized monoclonal antibody fragments (e.g., anti-αβTCR antibodies and/or fragments thereof) are also provided. Novel methods using repetitive administration of humanized monoclonal antibodies and/or humanized monoclonal antibody fragments (e.g., anti-αβTCR antibodies and/or fragments thereof) to reduce αβ T cells in the subject relative to γδ cells in the subject are provided.

11 Claims, 10 Drawing Sheets

Specification includes a Sequence Listing.

(56) References Cited

OTHER PUBLICATIONS

Sempe et al., Eur J Immunol. May 1991;21(5):1163-9. (Year: 1991).*
Michishita et al, Int J Hematol (2011) 94:230-240. (Year: 2011).*
Snell G. et al. (Drugs 2007; 67 (11): 1531-1539). (Year: 2007).*
Al-Lazikani et al. (1997) "Standard conformations for the canonical structures of immunoglobulins," J. Mol. Biol. 273:927-948.
Exner et al. (1999) "αβTCR+ T cells play a nonredundant role in the rejection of heart allografts in mice," Surgery. 126(2)121-126.
Giudicelli et al. (2011) "IMGT/V-Quest: IMGT Standardized Analysis of the Immunoglobulin (IG) and T Receptor (TR) Nucleotide Sequences," Cold Spring Harb Protoc. 2011(6):58-78.
Gu et al. (Nov. 22, 2013) "Rapamycin together with TGF-β1, IL-2 and IL-15 induces the generation of functional regulatory γσT cells from human peripheral blood mononuclear cells," J. Immunol. Meth. 402(1):82-87.
Heidecke et al. (1996) "Alpha-beta T Cell Receptor-directed Therapy in Rat Allograft Recipients," Transplantation. 61(6):948-956.
Heidecke et al. (1996) "Induction of Long-term Rat Renal Allograft Survival by Pretransplant T Cell Receptor Alpha-beta Targeted Therapy," Transplantation. 61(2):336-339.
Jung et al. (1992) "Prevention and Therapy of Experimental Autoimmune Neuritis by an Antibody Against T Cell Receptors-alpha-beta," Journal of Immunology. 148(12):3768-3775.
King et al. (2009) "Human peripheral blood leucocyte non-obese diabetic-severe combined immunodeficiency interleukin-2 receptor gamma chain gene mouse model of xenogeneic graft-versus-host-like disease and the role of host major histocompatibility complex," Clin. Exp. Immunol. 157(1):104-118.
Martin (2010) "Protein Sequence and Structure Analysis of Antibody Variable Domains," Ch. 3 In; Antibody Engineering. vol. 2. Eds: Kontermann et al. Springer-Verlag. Berlin. pp. 33-51.
North et al. (2011) "A new clustering of antibody CDR loop conformations," J. Mol. Biol. 406:228-256.
Page et al. (Jul. 2012) "Biologics in Organ Transplantation," Transplant International. 25:707-719.
Sazinsky et al. (2008) Proc. Natl. Acad. Sci. USA. 105(51):20167-20172.—with Supplementary Information.
Scharpf et al. (2006) "Immunomodulation with Anti-alpha-beta T Cell Receptor Monoclonal Antibodies in Combination With Cyclosporine A Improves Regeneration in Nerve Allografts," Microsurgery. 26:599-607.
Schorlemer et al. (1995) "Synergistic Effects of 15-Deoxyspergualin With Cyclosporine and the TCR-Targeted Monoclonal Antibody R73 to Induce Specific Unresponsiveness to Skin Allografts in Rats," Transplantation Proceedings. 27(1):414-416.
Shearman et al. (1991) "Construction, Expression, and Characterization of Humanized Antibodies Directed Against the Human Alpha-beta T Cell Receptor," Journal of Immunology. 147(12):4366-4373.
Williams et al. (2010) "Humanising Antibodies by CDR Grafting," Ch. 21 In; Antibody Engineering. vol. 1. Eds: Kontermann et al. Springer-Verlag. pp. 319-339.
Wright et al. (1992) "Genetically Engineered Antibodies: Progress and Prospects," Critical Reviews in Immunology. 12(3-4):125-168.
Yamagami et al. (1999) "Suppression of Allograft Rejection with Anti-alpha-beta T Cell Receptor Antibody in Rat Corneal Transplantation," Transplantation. 67(4):600-604.
Yoshino et al. (1992) "Depletion of Alpha-beta T Cells by a Monoclonal Antibody against the Alpha-beta T Cell Receptor Suppresses Established Adjuvant Arthritis, but not Established Collagen-induced Arthritis in Rats," J. Exp. Med. 175:907-915.
International Search Report with Written Opinion corresponding to International Patent Application No. PCT/EP2012/003819, dated Jun. 28, 2013.
International Search Report with Written Opinion corresponding to International Patent Application No. PCT/US2014/063254, dated May 4, 2015.
Do et al., "CD4 T Cells Play Important Roles in Maintaining IL-17-Producing γσ T Cell Subsets in Naïve Animals", Immunol. Cell Biol., Apr. 2012, vol. 90, No. 4, pp. 396-403.
Gonçalves-Sousa et al., "Inhibition of Murine σ6 Lymphocyte Expansion and Effector Function by Regulatory αβ T Cells is Cell-Contact-Dependent and Sensitive to GITR Modulation", Eur. J. Immunol., 2010, vol. 40, pp. 61-70.
He et al., "Yσ T Cell and Other Immune Cells Crosstalk in Cellular Immunity", Journal of Immunology Research, 2014, vol. 2014, Article ID 960252, pp. 1-8.
Spinozzi et al., "T Lymphocytes Bearing the γσ T Cell Receptor are Susceptible to Steroid-Induced Programmed Cell Death", Scand. J. Immunol., 1995, vol. 41, p. 504-508.
U.S. Appl. No. 14/241,099 / 2015/0099861, filed Nov. 18, 2014 / Apr. 9, 2015, Daniel Snell.

* cited by examiner

SEQUENCE LISTING

<160> NUMBER OF SEQ ID NOS: 25

<210> SEQ ID NO 1
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Lys Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Val Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val His Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ala
        115                 120

```
                115                 120

<210> SEQ ID NO 2
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 3
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Lys Phe Thr Ser Tyr
            20                  25                  30

Val Met His Trp Val Lys Gln Ala Pro Gly Gln Gly Leu Glu Trp Ile
        35                  40                  45

Gly Tyr Ile Asn Pro Tyr Asn Asp Val Thr Lys Tyr Asn Glu Lys Phe
    50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Val His Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 4
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

Synthetic polypeptide"

<400> SEQUENCE: 4

Asp Ile Gln Met Thr Gln Ser Pro Ser Thr Leu Ser Ala Ser Val Gly
1               5                   10                  15

Asp Arg Val Thr Met Thr Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ala Arg Phe Ile Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 5
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Lys Phe Thr Ser Tyr
            20                  25                  30

Val Met His Trp Val Lys Gln Ala Pro Gly Lys Gly Leu Glu Trp Ile
        35                  40                  45

Gly Tyr Ile Asn Pro Tyr Asn Asp Val Thr Lys Tyr Asn Glu Lys Phe
    50                  55                  60

Lys Gly Lys Ala Thr Leu Ser Arg Asp Asn Ser Lys Asn Thr Leu Tyr
65                  70                  75                  80

Leu Gln Met Asn Ser Leu Arg Ala Glu Asp Thr Ala Val His Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 6
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 6

Asp Ile Gln Met Thr Gln Ser Pro Ser Thr Leu Ser Ala Ser Val Gly
1               5                   10                  15

Asp Arg Val Thr Met Thr Cys Ser Ala Thr Ser Ser Val Ser Tyr Met
            20                  25                  30

```
His Trp Tyr Gln Gln Lys Pro Gly Lys Ala Pro Lys Arg Trp Ile Tyr
        35                  40                  45

Asp Thr Ser Lys Leu Ala Ser Gly Val Pro Ala Arg Phe Ile Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Gln Gln Trp Ser Ser Asn Pro Leu Thr
                 85                  90                  95

Phe Gly Gly Gly Thr Lys Val Glu Ile Lys
            100                 105
```

<210> SEQ ID NO 7
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Lys Phe Thr Ser Tyr
            20                  25                  30

Val Met His Trp Val Lys Gln Ala Pro Gly Lys Gly Leu Glu Trp Ile
        35                  40                  45

Gly Tyr Ile Asn Pro Tyr Asn Asp Val Thr Lys Tyr Asn Glu Lys Phe
 50                  55                  60

Lys Gly Lys Ala Thr Leu Ser Arg Asp Asn Ser Lys Asn Thr Leu Tyr
 65                  70                  75                  80

Leu Gln Met Asn Ser Leu Arg Ala Glu Asp Thr Ala Val His Tyr Cys
                 85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120
```

<210> SEQ ID NO 8
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Val Thr Lys Tyr Asn Glu Lys Phe
 50                  55                  60

Lys Gly Lys Ala Thr Ile Thr Arg Asp Thr Ser Ala Asn Thr Ala Tyr
 65                  70                  75                  80

Met Glu Leu Ser Ser Leu Arg Ser Glu Asp Thr Ala Val Tyr Tyr Cys
```

```
                        85                  90                  95

Ala Arg Gly Ser Tyr Tyr Asp Tyr Asp Gly Phe Val Tyr Trp Gly Gln
                    100                 105                 110

Gly Thr Leu Val Thr Val Ser Ser
            115                 120

<210> SEQ ID NO 9
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 10
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140
```

```
Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
            165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 11
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

-continued

Gly Val Glu Val His Asn Ala Lys Thr Lys Pro Arg Glu Glu Gln Phe
            165                 170                 175

Gln Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 12
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Glu Val Gln Leu Leu Gln Ser Gly Gly Gly Leu Val Gln Pro Gly Gly
1               5                   10                  15

Ser Leu Arg Leu Ser Cys Ala Ala Ser Gly Tyr Lys Phe Thr Ser Tyr
            20                  25                  30

Val Met His Trp Val Arg Gln Ala Pro Gly Lys Gly Leu Glu Trp Val
        35                  40                  45

Gly Tyr Ile Asn Pro Tyr Asn Asp Val Thr Lys Tyr Asn Glu Lys Phe
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 13
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Glu Val Gln Leu Leu Glu Ser Gly Gly Gly Leu Val Gln Pro Gly Gly
1               5                   10                  15

Ser Val Arg Leu Ser Cys Ala Ala Ser Gly Tyr Lys Phe Thr Ser Tyr
            20                  25                  30

Val Met His Trp Val Arg Gln Ala Pro Gly Lys Gly Leu Glu Trp Val
        35                  40                  45

Gly Tyr Ile Asn Pro Tyr Asn Asp Val Thr Lys Tyr Asn Glu Lys Phe
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 14
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Arg Leu Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 15
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Lys Gln Ala Pro Gly Gln Gly Leu Glu Trp Ile
        35                  40                  45

Gly Tyr Ile Asn Pro Tyr Asn Asp Val Thr Lys Tyr Asn Glu Lys Phe
            50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
                115                 120

<210> SEQ ID NO 16
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Lys Phe Thr Ser Tyr
                 20                  25                  30

Val Met His Trp Val Arg Gln Ala Pro Gly Gln Gly Leu Glu Trp Ile
             35                  40                  45

Gly Tyr Ile Asn Pro Tyr Asn Asp Val Thr Lys Tyr Asn Glu Lys Phe
        50                   55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
                115                 120

<210> SEQ ID NO 17
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
        50                   55                  60

Lys Gly Arg Phe Thr Ile Ser Arg Asp Asn Ser Lys Asn Thr Leu Tyr
 65                  70                  75                  80

```
Leu Gln Met Asn Ser Leu Arg Ala Glu Asp Thr Ala Val Tyr Tyr Cys
                85                  90                  95

Ala Lys

<210> SEQ ID NO 18
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 19
<211> LENGTH: 95
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 20
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Val Thr Lys Tyr Asn Glu Lys Phe
    50                  55                  60

Lys Gly Lys Ala Thr Ile Thr Arg Asp Thr Ser Ala Ser Thr Ala Tyr
65              70                  75                  80

Met Glu Leu Ser Ser Leu Arg Ser Glu Asp Thr Ala Val Tyr Tyr Cys
            85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
            115                 120

<210> SEQ ID NO 21
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65              70                  75                  80

Asp Phe Ala Val Tyr Tyr Cys Gln Gln Trp Ser Ser Asn Pro Leu Thr
            85                  90                  95

Phe Gly Gly Gly Thr Lys Val Glu Ile Lys
            100                 105

<210> SEQ ID NO 22
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser

```
                    50                  55                  60
Gly Ser Gly Thr Asp Phe Thr Leu Thr Ile Ser Ser Met Glu Pro Glu
 65                  70                  75                  80

Asp Phe Ala Val Tyr Tyr Cys Gln Gln Trp Ser Ser Asn Pro Leu Thr
                     85                  90                  95

Phe Gly Gly Gly Thr Lys Val Glu Ile Lys
                100                 105

<210> SEQ ID NO 23
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Lys Phe Thr Ser Tyr
                 20                  25                  30

Val Met His Trp Val Lys Gln Lys Pro Gly Gln Gly Leu Glu Trp Ile
             35                  40                  45

Gly Tyr Ile Asn Pro Tyr Asn Asp Val Thr Lys Tyr Asn Glu Lys Phe
         50                  55                  60

Lys Gly Lys Ala Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120

<210> SEQ ID NO 24
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Lys Phe Thr Ser Tyr
                 20                  25                  30

Val Met His Trp Val Lys Gln Ala Pro Gly Gln Gly Leu Glu Trp Ile
             35                  40                  45

Gly Tyr Ile Asn Pro Tyr Asn Asp Val Thr Lys Tyr Asn Glu Lys Phe
         50                  55                  60

Lys Gly Lys Ala Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Asp Tyr Asp Gly Phe Val Tyr Trp Gly Gln
                100                 105                 110
```

```
Gly Thr Leu Val Thr Val Ser Ser
        115             120

<210> SEQ ID NO 25
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 25

His His His His His His
1               5
```

METHODS FOR ENHANCING IMMUNOSUPPRESSIVE THERAPY BY MULTIPLE ADMINISTRATION OF αβTCR-BINDING POLYPEPTIDE

RELATED APPLICATIONS

This application is a 35 U.S.C. § 371 filing of International Application No. PCT/US2014/063254, filed Oct. 30, 2014, which claims priority to U.S. Ser. No. 61/897,809, filed on Oct. 30, 2013, the contents of each of which are incorporated herein by reference in their entireties for all purposes.

BACKGROUND

Solid organ transplantation and stem cell transplantation are lifesaving techniques now used on a daily basis around the world. Despite decades of research into immunoprophylaxis, the use of immunosuppressive agents to prevent rejection of these transplants is still far from optimal. Toxicity, opportunistic infections, cytokine storm and an increased risk of cancer are prevalent in patients treated with these agents, who often require lifelong immunosuppression. The use of biologics in this arena has improved patient outcome to some degree, yet these side effects continue to present great difficulties for patients and doctors.

Alpha/beta T lymphocytes recognize peptide-MHC ligands by means of a multimeric protein ensemble termed the αβ T cell antigen receptor (TCR)-CD3 complex. This structure is composed of a variable αβ TCR dimer which binds antigens, and three invariant dimers (CD3γε, δε, and ζζ) which are involved in TCR-CD3 surface transport, stabilization and signal transduction. The alpha beta T cell receptor (αβ TCR) is expressed on the majority (approximately 95%) of T cells and has a critical role in T cell activation via engagement of antigen displayed on MHC. New humanized monoclonal antibodies targeting the αβTCR cells have been developed that show improved binding profiles (WO2013037484). These promising new antibodies (described both in WO2013037484 and herein) include GL1BM VH31, GL1BM VH28, HEBE1 H66, and HEBE1 H71. There is a need in the art for improved methods of administration of this type of humanized anti-αβTCR antibody which can counter alloreactive T lymphocytes while sparing pathogen inactive T cells (such as γδ T-cells, iNK T cells, and CD3-CD56+ NK cells).

SUMMARY

The present invention is based in part on the surprising discovery that repetitive administration of humanized anti-αβTCR-binding polypeptide to a subject resulted in a significant reduction of αβ T cells relative to γδ T cells in the subject. Importantly, by increasing γδ T cell levels relative to αβ T cells in the subject, one or more advantageous innate and adaptive immune features provided by γδ T cells could be enhanced in the subject. Retaining γδ T cell-mediated immunity is particularly important, e.g., when treating a T-cell mediated disorder in a subject, optionally when using transplanted cells, tissues, organs or the like. The present invention also demonstrates the effectiveness of humanized monoclonal antibodies targeting the αβTCR both in vitro and in vivo. Improved methods for the use monoclonal antibodies targeting the αβTCR are also provided.

In one embodiment, the disclosure teaches a method of preferentially reducing αβ T cells (e.g., human αβ T cells) relative to γδ T cells (e.g., human γδ T cells) in a subject comprising administering a humanized anti-αβTCR binding polypeptide to the subject in two, three or more doses. In another embodiment, the doses are sequential doses. In another embodiment, the human αβ T cells that are most preferentially reduced are CD4+ human αβ T cells. In another embodiment, preferential reduction of αβ T cells relative to γδ T cells occurs in one or any combination of peripheral blood cells, the spleen and bone marrow. In another embodiment, the subject has or is at risk of having a T cell-mediated disorder. In another embodiment, the T cell-mediated disorder arises due to a cell, tissue, body part, or organ transplantation. In another embodiment, the T cell-mediated disorder is selected from the group consisting of an autoimmune disorder, a xenotransplant-related disorder, an allotransplant-related disorder, a xenopregnancy-related disorder, pre-eclampsia, and Rh disease. In another embodiment, the humanized anti-αβTCR binding polypeptide is a humanized monoclonal antibody. In another embodiment, the humanized monoclonal antibody is GL1BM VH31, GL1BM VH28, HEBE1 H66, or HEBE1 H71.

In one embodiment, the disclosure teaches a method of preferentially reducing αβ T cells relative to γδ T cells in peripheral blood of a subject, comprising administering to the subject a humanized anti-αβTCR binding polypeptide in two or more doses. In another embodiment, the subject has or is at risk of having a T cell-mediated disorder. In another embodiment, the T cell-mediated disorder arises due to a cell, tissue, body part, or organ transplantation. In another embodiment, the T cell-mediated disorder is selected from the group consisting of an autoimmune disorder, a xenotransplant-related disorder, an allotransplant-related disorder, a xenopregnancy-related disorder, pre-eclampsia, and Rh disease. In another embodiment, the T cell-mediated disorder is selected from the group consisting of systemic lupus erythematosus (SLE), rheumatoid arthritis (RA) and inflammatory bowel disease (IBD) (including ulcerative colitis (UC) and Crohn's disease (CD)), multiple sclerosis (MS), scleroderma and type 1 diabetes (T1D), and other diseases and disorders, such as pemphigus vulgaris (PV), psoriasis, atopic dermatitis, celiac disease, chronic obstructive lung disease, Hashimoto's thyroiditis, Graves' disease (thyroid), Sjogren's syndrome, Guillain-Barre syndrome, Goodpasture's syndrome, Addison's disease, Wegener's granulomatosis, primary biliary sclerosis, sclerosing cholangitis, autoimmune hepatitis, polymyalgia rheumatica, Raynaud's phenomenon, temporal arteritis, giant cell arteritis, autoimmune hemolytic anemia, pernicious anemia, polyarteritis nodosa, behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia areata, and vitilgo. In another embodiment, the humanized anti-αβTCR binding polypeptide is a humanized monoclonal antibody. In another embodiment, the humanized monoclonal antibody is GL1BM VH31, GL1BM VH28, HEBE1 H66, or HEBE1 H71.

In one embodiment, the disclosure teaches a method of preferentially reducing αβ T cells relative to γδ T cells in the spleen of a subject, comprising administering to the subject a humanized anti-αβTCR binding polypeptide in two or more doses. In another embodiment, the subject has or is at risk of having a T cell-mediated disorder. In another embodiment, the T cell-mediated disorder arises due to a cell, tissue, body part, or organ transplantation. In another embodiment, the T cell-mediated disorder is selected from the group consisting of an autoimmune disorder, a xenotransplant-related disorder, an allotransplant-related disorder, a xenopregnancy-related disorder, pre-eclampsia, and Rh disease. In another embodiment, the T cell-mediated disorder is selected from the group consisting of systemic lupus erythematosus (SLE), rheumatoid arthritis (RA) and inflammatory bowel disease (IBD) (including ulcerative colitis (UC) and Crohn's disease (CD)), multiple sclerosis (MS), scleroderma and type 1 diabetes (T1D), and other diseases and disorders, such as pemphigus vulgaris (PV), psoriasis, atopic dermatitis, celiac disease, chronic obstructive lung disease, Hashimoto's thyroiditis, Graves' disease (thyroid), Sjogren's syndrome, Guillain-Barre syndrome, Goodpasture's syndrome, Addison's disease, Wegener's granulomatosis, primary biliary sclerosis, sclerosing cholangitis, autoimmune hepatitis, polymyalgia rheumatica, Raynaud's phenomenon, temporal arteritis, giant cell arteritis, autoimmune hemolytic anemia, pernicious anemia, polyarteritis nodosa, behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia areata, and vitilgo. In another embodiment, the humanized anti-αβTCR binding polypeptide is a humanized monoclonal antibody. In another embodiment, the humanized monoclonal antibody is GL1BM VH31, GL1BM VH28, HEBE1 H66, or HEBE1 H71.

In one embodiment, the disclosure teaches a method of preferentially reducing αβ T cells relative to γδ T cells in the bone marrow of a subject, comprising administering to the subject a humanized anti-αβTCR binding polypeptide in two or more doses. In another embodiment, the subject has or is at risk of having a T cell-mediated disorder. In another embodiment, the T cell-mediated disorder arises due to a cell, tissue, body part, or organ transplantation. In another embodiment, the T cell-mediated disorder is selected from the group consisting of an autoimmune disorder, a xenotransplant-related disorder, an allotransplant-related disorder, a xenopregnancy-related disorder, pre-eclampsia, and Rh disease. In another embodiment, the T cell-mediated disorder is selected from the group consisting of systemic lupus erythematosus (SLE), rheumatoid arthritis (RA) and inflammatory bowel disease (IBD) (including ulcerative colitis (UC) and Crohn's disease (CD)), multiple sclerosis (MS), scleroderma and type 1 diabetes (T1D), and other diseases and disorders, such as pemphigus vulgaris (PV), psoriasis, atopic dermatitis, celiac disease, chronic obstructive lung disease, Hashimoto's thyroiditis, Graves' disease (thyroid), Sjogren's syndrome, Guillain-Barre syndrome, Goodpasture's syndrome, Addison's disease, Wegener's granulomatosis, primary biliary sclerosis, sclerosing cholangitis, autoimmune hepatitis, polymyalgia rheumatica, Raynaud's phenomenon, temporal arteritis, giant cell arteritis, autoimmune hemolytic anemia, pernicious anemia, polyarteritis nodosa, behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia areata, and vitilgo. In another embodiment, the humanized anti-αβTCR binding polypeptide is a humanized monoclonal antibody. In another embodiment, the humanized monoclonal antibody is GL1BM VH31, GL1BM VH28, HEBE1 H66, or HEBE1 H71.

In another embodiment, the disclosure teaches a method of increasing the proportion of γδ T cells within the CD3+ T cell population in a subject, comprising administering to the subject a humanized anti-αβTCR binding polypeptide in two, three or more doses. In another embodiment, the subject has or is at risk of having a T cell-mediated disorder. In another embodiment, the T cell-mediated disorder arises due to a cell, tissue, body part, or organ transplantation. In another embodiment, the T cell-mediated disorder is selected from the group consisting of an autoimmune disorder, a xenotransplant-related disorder, an allotransplant-related disorder, a xenopregnancy-related disorder, pre-eclampsia, and Rh disease. In another embodiment, the T cell-mediated disorder is selected from the group consisting of systemic lupus erythematosus (SLE), rheumatoid arthritis (RA) and inflammatory bowel disease (IBD) (including ulcerative colitis (UC) and Crohn's disease (CD)), multiple sclerosis (MS), scleroderma and type 1 diabetes (T1D), and other diseases and disorders, such as pemphigus vulgaris (PV), psoriasis, atopic dermatitis, celiac disease, chronic obstructive lung disease, Hashimoto's thyroiditis, Graves' disease (thyroid), Sjogren's syndrome, Guillain-Barre syndrome, Goodpasture's syndrome, Addison's disease, Wegener's granulomatosis, primary biliary sclerosis, sclerosing cholangitis, autoimmune hepatitis, polymyalgia rheumatica, Raynaud's phenomenon, temporal arteritis, giant cell arteritis, autoimmune hemolytic anemia, pernicious anemia, polyarteritis nodosa, behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia areata, and vitilgo. In another embodiment, the humanized anti-αβTCR binding polypeptide is a humanized monoclonal antibody. In another embodiment, the humanized monoclonal antibody is GL1BM VH31, GL1BM VH28, HEBE1 H66, or HEBE1 H71.

In another embodiment, the disclosure teaches a method of sparing pathogen inactive cells while suppressing a T cell mediated response in a subject in need thereof comprising administering multiple doses of a humanized anti-αβTCR binding polypeptide to the subject. In a further embodiment, the pathogen inactive cells selected from the group consisting of CD3+ effector cells, γδ T cells, iNK T cells and NK cells. In another embodiment, the humanized anti-αβTCR binding polypeptide is a humanized monoclonal antibody. In another embodiment, the humanized monoclonal antibody is GL1BM VH31, GL1BM VH28, HEBE1 H66, or HEBE1 H71.

In another embodiment, the disclosure teaches a method of specifically eliminating alloreactive T cells in a subject comprising the steps of administering to the subject a humanized anti-αβTCR binding polypeptide in two, three or more doses. In another embodiment, the humanized anti-αβTCR binding polypeptide is a humanized monoclonal antibody. In another embodiment, the humanized monoclonal antibody is GL1BM VH31, GL1BM VH28, HEBE1 H66, or HEBE1 H71.

In another embodiment, the disclosure teaches a method for enhancing one or both of innate immunity and adaptive immunity in a subject undergoing T cell reduction comprising the steps of administering to the subject a humanized anti-αβTCR binding polypeptide in two, three or more doses, and preferentially reducing αβ T cells relative to γδ T cells in the subject to enhance one or both of innate immunity and adaptive immunity in the subject. In another embodiment, preferential reduction of αβ T cells relative to γδ T cells occurs in one or any combination of peripheral blood cells, the spleen and the bone marrow. In another embodiment, enhancement one or both of innate immunity and adaptive immunity in a first subject undergoing preferential reducing αβ T cells relative to γδ T cells is determined relative to a second subject undergoing non-preferential reduction of αβ T cells, e.g., undergoing a generalized T cell reduction. In another embodiment, the humanized anti-αβTCR binding polypeptide is a humanized monoclonal antibody. In another embodiment, the humanized monoclonal antibody is GL1BM VH31, GL1BM VH28, HEBE1 H66, or HEBE1 H71.

In one embodiment, this disclosure teaches a method of treating a T-cell mediated disorder that arises due to a cell, tissue, body part, or organ transplantation in a subject in need thereof comprising transplanting a cell, tissue, body part, or organ into the subject and administering two, three or more doses of a pharmaceutically acceptable amount of a humanized anti-αβTCR binding polypeptide to the subject. In another embodiment, the humanized anti-αβTCR binding polypeptide is a humanized monoclonal antibody. In another embodiment, the humanized monoclonal antibody is GL1BM VH31, GL1BM VH28, HEBE1 H66, or HEBE1 H71.

In another embodiment, the disclosure teaches a method of treating a T-cell mediated disorder in a subject in need thereof comprising administering a pharmaceutically acceptable amount of a humanized anti-αβTCR binding polypeptide to the subject in two, three or more doses. In a further embodiment, the T-cell mediated disorder is selected from the group consisting of an autoimmune disorder, a xenotransplant-related disorder, an allotransplant-related disorder, a xenopregnancy-related disorder, pre-eclampsia and Rh disease. In embodiments, the T cell-mediated disorder is selected from the group consisting of systemic lupus erythematosus (SLE), rheumatoid arthritis (RA) and inflammatory bowel disease (IBD) (including ulcerative colitis (UC) and Crohn's disease (CD)), multiple sclerosis (MS), scleroderma and type 1 diabetes (T1D), and other diseases and disorders, such as pemphigus vulgaris (PV), psoriasis, atopic dermatitis, celiac disease, chronic obstructive lung disease, Hashimoto's thyroiditis, Graves' disease (thyroid), Sjogren's syndrome, Guillain-Barre syndrome, Goodpasture's syndrome, Addison's disease, Wegener's granulomatosis, primary biliary sclerosis, sclerosing cholangitis, autoimmune hepatitis, polymyalgia rheumatica, Raynaud's phenomenon, temporal arteritis, giant cell arteritis, autoimmune hemolytic anemia, pernicious anemia, polyarteritis nodosa, behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia areata, and vitilgo.

In certain embodiments, one or more doses of a humanized monoclonal antibody, or a humanized monoclonal antibody fragment (e.g., an anti-αβTCR antibody or fragment thereof) may be administered to a subject, e.g., to preferentially reduce αβ T cells relative to γδ T cells in a subject, to increase the proportion of γδ T cells within a CD3+ T cell population in a subject, to spare pathogen inactive cells while suppressing a T cell-mediated response in a subject, to specifically eliminating alloreactive T cells in a subject, to enhance one or both of innate immunity and adaptive immunity in a subject undergoing T cell reduction, to treat a T cell-mediated disorder in a subject, or any combination of these. A pharmaceutically acceptable amount of a humanized monoclonal antibody, or a humanized monoclonal antibody fragment (e.g., an anti-αβTCR antibody or fragment thereof) may be administered subject in one or more doses using any means, including but not limited to any and all of the methods and compositions described herein.

In certain embodiments, a humanized monoclonal antibody, or a humanized monoclonal antibody fragment (e.g., an anti-αβTCR antibody or fragment thereof) may be administered to a subject multiple times. The multiple doses of a humanized monoclonal antibody, or a humanized monoclonal antibody fragment (e.g., an anti-αβTCR antibody or fragment thereof) may be given for a defined period of time (e.g. one week, one month, 6 months, one year, 5 years, or 10 years), e.g., for a period of time equal to the duration of or risk for a disease, disorder, or illness requiring treatment, or for the entire life of the subject. The second and subsequent doses of a humanized monoclonal antibody, or a humanized monoclonal antibody fragment (e.g., an anti-αβTCR antibody or fragment thereof) may be administered to the subject immediately after administration of the first dose (0 to 10 minutes after, including 1, 2, 3, 4, 5, 6, 7, 8, 9 or 10 minutes after), within one hour after administration of the first dose (e.g., 15, 20, 25, 30, 35, 40, 45, 50, 55, or 60 minutes after), within one day after administration of the first dose (e.g. 1, 2, 3, 4, 5, 6, 7, 8, 9, 10, 11, 12, 13, 14, 15, 16, 17, 18, 19, 20, 21, 22, 23, or 24 hours after), within one week administration of the first dose (e.g. within 1, 2, 3, 4, 5, 6, or 7 days after), within one month after administration of the first dose (e.g. 1, 2, 3, or 4 weeks), within 6 months (e.g. within 1, 2, 3, 4, 5, or 6 months) after administration of the first dose, etc. The second and subsequent doses may be given at regular intervals including but not limited to daily, weekly, monthly, or yearly. The doses may be administered more frequently within the first days, weeks or months after transplantation or the interval between doses may remain the same.

In some embodiments, the number of doses may range from, but is not limited to, between two and several thousand doses. For example, the number of doses a subject receives may be: between 2 and 10 doses, (i.e.: there may be 2, 3, 4, 5, 6, 7, 9, or 10 doses) administered; between 11 and 20 doses (i.e. there may be 11, 12, 13, 14, 15, 16, 17, 18, 19, or 20 doses) administered, between 21 and 30 doses (i.e. there may be 21, 22, 23, 24, 25, 26, 27, 28, 29, or 30 doses) administered, between 31 and 40 doses (i.e. there may be 31, 32, 33, 34, 35, 36, 37, 38, 39, or 40 doses) administered, between 41 and 50 doses (i.e. there may be 31, 32, 33, 34, 35, 36, 37, 38, 39, or 50 doses) administered, between 51 and 60 doses (i.e. there may be 51, 52, 53, 54, 55, 56, 57, 58, 59, or 60 doses) administered, between 61 and 70 doses (i.e. there may be 61, 62, 63, 64, 65, 66, 67, 68, 69, or 70 doses) administered, between 71 and 80 doses (i.e. there may be 71, 72, 73, 74, 75, 76, 77, 78, 79, or 80 doses) administered, between 81 and 90 doses (i.e. there may be 81, 82, 83, 84, 85, 86, 87, 88, 89, or 90 doses) administered, or between 91 and 100 doses (i.e. there may be 91, 92, 93, 94, 95, 96, 97, 98, 99, or 100 doses) administered. The number of doses a subject receives may also be in excess of 100 doses, e.g. it may be between 101 and 200 doses, between 201 and 300 doses, between 301 and 400 doses, between 401 and 500 doses, between 501 and 600 doses, between 601 and 700 doses, between 701 and 800 doses, between 801 and 900 doses, between 901 and 1,000 doses, 1,100 and 1,200 doses, between 1,201 and 1,300 doses, between 1,301 and 1,400 doses, between 1,401 and 1,500 doses, between 1,501 and 1,600 doses, between 1,601 and 1,700 doses, between 1,701 and 1,800 doses, between 1,801 and 1,900 doses, and between 1,901 and 2,000 doses, 2,100 and 2,200 doses, between 2,201 and 2,300 doses, between 2,301 and 2,400 doses, between 2,401 and 2,500 doses, between 2,501 and 2,600 doses, between 2,601 and 2,700 doses, between 2,701 and 2,800 doses, between 2,801 and 2,900 doses, and between 2,901 and 3,000 doses, 3,100 and 3,200 doses, between 3,201 and 3,300 doses, between 3,301 and 3,400 doses, between 3,401 and 3,500 doses, between 3,501 and 3,600 doses, between 3,601 and 3,700 doses, between 3,701 and 3,800 doses, between 3,801 and 3,900 doses, and between 3,901 and 4,000 doses, 4,100 and 4,200 doses, between 4,201 and 4,300 doses, between 4,301 and 4,400 doses, between 4,401 and 4,500 doses, between 4,501 and 4,600 doses, between 4,601 and 4,700 doses, between 4,701 and 4,800 doses, between 4,801 and 4,900 doses, and between 4,901 and 5,000 doses. Depending on the severity of the case and the length of time the subject is in need of the medication, the number of doses could also exceed 5,000 and may, for example, number about 6,000, about 7,000, about 8,000, about 9,000, or about 10,000.

In embodiments, there may be one or more doses of a humanized monoclonal antibody, or a humanized monoclonal antibody fragment (e.g., an anti-αβTCR antibody or fragment thereof) administered during treatment for a T-cell mediated disorder, or after treatment for a T-cell mediated disorder or advent of risk for a T-cell mediated disorder. A humanized monoclonal antibody, or a humanized monoclonal antibody fragment (e.g., an anti-αβTCR antibody or fragment thereof) may be administered only prior to advent of risk for T-cell mediated disorder, only during advent of risk for T-cell mediated disorder, or only after advent of risk for T-cell mediated disorder. A humanized monoclonal antibody, or a humanized monoclonal antibody fragment (e.g., an anti-αβTCR antibody or fragment thereof) may also be administered before and during advent of risk for T-cell mediated disorder, during and after advent of risk for T-cell mediated disorder, before and after advent of risk for T-cell mediated disorder, or before, during and after advent of risk for T-cell mediated disorder. There may be one or more than one dose of a humanized monoclonal antibody, or a humanized monoclonal antibody fragment (e.g., an anti-αβTCR antibody or fragment thereof) administered during each of these periods. For example, there may be one or more than one dose administered before and during advent of risk for T-cell mediated disorder, one or more than one dose administered during and after advent of risk for T-cell mediated disorder, one or more than one dose administered before and after advent of risk for T-cell mediated disorder, or one or more than one dose administered before, during, and after advent of risk for T-cell mediated disorder. The number of doses during any of these periods may range from, but is not limited to, between two and several thousand doses as discussed further herein.

In certain embodiments, one or more doses a humanized monoclonal antibody, or a humanized monoclonal antibody fragment (e.g., an anti-αβTCR antibody or fragment thereof) may be administered to a cell, tissue, body part, or solid organ before it is transplanted into the subject. This administration may occur, for example, in vivo (prior to explantation or extraction), ex vivo (post explantation or extraction), or in vitro (post explantation or extraction). A pharmaceutically acceptable amount of a humanized monoclonal antibody, or a humanized monoclonal antibody fragment (e.g., an anti-αβTCR antibody or fragment thereof) may be administered to the cell, tissue, body part, or solid organ using any means, including but not limited to any and all of the methods and compositions discussed above. A humanized monoclonal antibody, or a humanized monoclonal antibody fragment (e.g., an anti-αβTCR antibody or fragment thereof) may be administered to the cell, tissue, body part, or solid organ in any manner including, but not limited to: cell culture, perfusion, injection, immersion, and infusion. This administration may be performed in any suitable environment, including but not limited to: a dish, a bioreactor, and/or a culture chamber. In certain embodiments, the administration of a humanized monoclonal antibody, or a humanized monoclonal antibody fragment (e.g., an anti-αβTCR antibody or fragment thereof) prior to transplantation may occur through administration to the donor organism.

In certain embodiments, a humanized monoclonal antibody, or a humanized monoclonal antibody fragment (e.g., an anti-αβTCR antibody or fragment thereof) may be administered to a subject in need thereof multiple times after the transplantation of a cell, tissue, body part, or organ into the subject. The multiple doses of a humanized monoclonal antibody, or a humanized monoclonal antibody fragment (e.g., an anti-αβTCR antibody or fragment thereof) may be given for a defined period of time (e.g. one week, one month, 6 months, one year, 5 years, or 10 years), for a period of time equal to the duration of or risk for the disease, disorder, or illness requiring treatment, or for the entire life of the subject. The first dose of a humanized monoclonal antibody, or a humanized monoclonal antibody fragment (e.g., an anti-αβTCR antibody or fragment thereof) may be administered to the subject concurrently with the transplantation, immediately after the transplantation (0 to 10 minutes after, including 1, 2, 3, 4, 5, 6, 7, 8, 9 or 10 minutes after), within one hour after the transplantation (e.g., 15, 20, 25, 30, 35, 40, 45, 50, 55, or 60 minutes after), within one day after the transplantation (e.g. 1, 2, 3, 4, 5, 6, 7, 8, 9, 10, 11, 12, 13, 14, 15, 16, 17, 18, 19, 20, 21, 22, 23, or 24 hours after), within one week after the transplantation (e.g. within 1, 2, 3, 4, 5, 6, or 7 days after), within one month after transplantation (e.g. 1, 2, 3, or 4 weeks), or within 6 months (e.g. within 1, 2, 3, 4, 5, or 6 months) after transplantation. The second and subsequent doses of a humanized monoclonal antibody, or a humanized monoclonal antibody fragment (e.g., an anti-αβTCR antibody or fragment thereof) may be administered to the subject immediately after the transplantation (0 to 10 minutes after, including 1, 2, 3, 4, 5, 6, 7, 8, 9 or 10 minutes after), within one hour after the transplantation (e.g., 15, 20, 25, 30, 35, 40, 45, 50, 55, or 60 minutes after), within one day after the transplantation (e.g. 1, 2, 3, 4, 5, 6, 7, 8, 9, 10, 11, 12, 13, 14, 15, 16, 17, 18, 19, 20, 21, 22, 23, or 24 hours after), within one week after the transplantation (e.g. within 1, 2, 3, 4, 5, 6, or 7 days after), within one month after transplantation (e.g. 1, 2, 3, or 4 weeks), or within 6 months (e.g. within 1, 2, 3, 4, 5, or 6 months) after transplantation. The second and subsequent doses may be given at regular intervals including but not limited to daily, weekly, monthly, or yearly. The doses may be administered more frequently within the first days, weeks or months after transplantation or the interval between doses may remain the same.

In some embodiments, the number of doses may range from, but is not limited to, between 2 and several thousand doses. For example, the number of doses a subject receives may be: between 2 and 10 doses, (i.e.: there may be 2, 3, 4, 5, 6, 7, 9, or 10 doses) administered; between 11 and 20 doses (i.e. there may be 11, 12, 13, 14, 15, 16, 17, 18, 19, or 20 doses) administered, between 21 and 30 doses (i.e. there may be 21, 22, 23, 24, 25, 26, 27, 28, 29, or 30 doses) administered, between 31 and 40 doses (i.e. there may be 31, 32, 33, 34, 35, 36, 37, 38, 39, or 40 doses) administered, between 41 and 50 doses (i.e. there may be 31, 32, 33, 34, 35, 36, 37, 38, 39, or 50 doses) administered, between 51 and 60 doses (i.e. there may be 51, 52, 53, 54, 55, 56, 57, 58, 59, or 60 doses) administered, between 61 and 70 doses (i.e.

there may be 61, 62, 63, 64, 65, 66, 67, 68, 69, or 70 doses) administered, between 71 and 80 doses (i.e. there may be 71, 72, 73, 74, 75, 76, 77, 78, 79, or 80 doses) administered, between 81 and 90 doses (i.e. there may be 81, 82, 83, 84, 85, 86, 87, 88, 89, or 90 doses) administered, or between 91 and 100 doses (i.e. there may be 91, 92, 93, 94, 95, 96, 97, 98, 99, or 100 doses) administered. The number of doses a subject receives may also be in excess of 100 doses, e.g. it may be between 101 and 200 doses, between 201 and 300 doses, between 301 and 400 doses, between 401 and 500 doses, between 501 and 600 doses, between 601 and 700 doses, between 701 and 800 doses, between 801 and 900 doses, between 901 and 1,000 doses, 1,100 and 1,200 doses, between 1,201 and 1,300 doses, between 1,301 and 1,400 doses, between 1,401 and 1,500 doses, between 1,501 and 1,600 doses, between 1,601 and 1,700 doses, between 1,701 and 1,800 doses, between 1,801 and 1,900 doses, and between 1,901 and 2,000 doses, 2,100 and 2,200 doses, between 2,201 and 2,300 doses, between 2,301 and 2,400 doses, between 2,401 and 2,500 doses, between 2,501 and 2,600 doses, between 2,601 and 2,700 doses, between 2,701 and 2,800 doses, between 2,801 and 2,900 doses, and between 2,901 and 3,000 doses, 3,100 and 3,200 doses, between 3,201 and 3,300 doses, between 3,301 and 3,400 doses, between 3,401 and 3,500 doses, between 3,501 and 3,600 doses, between 3,601 and 3,700 doses, between 3,701 and 3,800 doses, between 3,801 and 3,900 doses, and between 3,901 and 4,000 doses, 4,100 and 4,200 doses, between 4,201 and 4,300 doses, between 4,301 and 4,400 doses, between 4,401 and 4,500 doses, between 4,501 and 4,600 doses, between 4,601 and 4,700 doses, between 4,701 and 4,800 doses, between 4,801 and 4,900 doses, and between 4,901 and 5,000 doses. Depending on the severity of the case and the length of time the subject is in need of the medication, the number of doses could also exceed 5,000 and may, for example, number about 6,000, about 7,000, about 8,000, about 9,000, or about 10,000.

In embodiments, there may be one or more doses of a humanized monoclonal antibody, or a humanized monoclonal antibody fragment (e.g., an anti-αβTCR antibody or fragment thereof) administered before the transplant or advent of risk for T-cell mediated disorder, during the transplant or advent of risk for T-cell mediated disorder, or after the transplant or advent of risk for T-cell mediated disorder. A humanized monoclonal antibody, or a humanized monoclonal antibody fragment (e.g., an anti-αβTCR antibody or fragment thereof) may be administered only prior to the transplant or advent of risk for T-cell mediated disorder, only during the transplant or advent of risk for T-cell mediated disorder, or only after the transplant or advent of risk for T-cell mediated disorder. A humanized monoclonal antibody, or a humanized monoclonal antibody fragment (e.g., an anti-αβTCR antibody or fragment thereof) may also be administered before and during the transplant or advent of risk for T-cell mediated disorder, during and after the transplant or advent of risk for T-cell mediated disorder, before and after the transplant or advent of risk for T-cell mediated disorder, or before, during, and after the transplant or advent of risk for T-cell mediated disorder. There may be one or more than one dose of a humanized monoclonal antibody, or a humanized monoclonal antibody fragment (e.g., an anti-αβTCR antibody or fragment thereof) administered during each of these periods. For example, there may be one or more than one dose administered before and during the transplant or advent of risk for T-cell mediated disorder, one or more than one dose administered during and after the transplant or advent of risk for T-cell mediated disorder, one or more than one dose administered before and after the transplant or advent of risk for T-cell mediated disorder, or one or more than one dose administered before, during, and after the transplant or advent of risk for T-cell mediated disorder. The number of doses during any of these periods may range from, but is not limited to, between 2 and several thousand doses as discussed Supra. All described dosage and treatment regimens described herein may be administered to either the donor or the recipient.

In any of the above aspects and embodiments, the humanized anti-αβTCR binding polypeptide can be a humanized monoclonal antibody described in WO2013037484, including but not limited to GL1BM VH31, GL1BM VH28, HEBE1 H66, and HEBE1 H71. WO2013037484 is incorporated herein in its entirety for all purposes.

In a particular embodiment, the humanized anti-αβTCR binding polypeptide is a humanized monoclonal antibody comprising a heavy chain variable region selected from the heavy chains comprising the amino acid sequences set forth in SEQ ID NO: 15 and SEQ ID NO: 16, and the light chain variable region comprising the amino acid sequence as set forth in SEQ ID NO: 14.

In a particular embodiment, the humanized anti-αβTCR binding polypeptide is a humanized monoclonal antibody comprising a heavy chain variable region comprising the CDRs set forth in SEQ ID NO: 15 and SEQ ID NO: 16, and the human IGHV1-3*01 framework set forth in SEQ ID NO: 18, wherein one or more of framework positions 38, 44, and 48 are donor residues.

In a particular embodiment, the humanized anti-αβTCR binding polypeptide is a humanized monoclonal antibody comprising a light chain variable region comprising the CDRs set forth in SEQ ID NO: 14 and the human IGKV3-11*01 framework set forth in SEQ ID NO: 19, wherein one or more of framework positions 46, 70, and 71 are donor residues.

In a particular embodiment, the humanized anti-αβTCR binding polypeptide is a humanized monoclonal antibody comprising a heavy chain variable region comprising the CDRs set forth in SEQ ID NOs: 7, 12, or 13 and the human IGH3-23 framework as set forth in SEQ ID NO: 17, wherein one or more of framework positions 6, 18, 49, and 69 are donor residues.

In a particular embodiment, the humanized anti-αβTCR binding polypeptide is a humanized monoclonal antibody comprising a heavy chain variable region selected from the heavy chains comprising the amino acid sequences set forth in SEQ ID NO: 7, SEQ ID NO: 12, and SEQ ID NO: 13, and the light chain variable region sequence comprising the amino acid sequence as set forth in SEQ ID NO: 14.

In a particular embodiment, a humanized anti-αβTCR binding polypeptide for use in the methods described here is provided. In another embodiment, the humanized anti-αβTCR binding polypeptide is a humanized monoclonal antibody or fragment thereof.

In another embodiment, the humanized monoclonal antibody or fragment thereof is GL1BM VH31, GL1BM VH28, HEBE1 H66, or HEBE1 H71. In another embodiment, the humanized monoclonal antibody or fragment thereof comprises a heavy chain variable region comprising the amino acid sequence set forth in SEQ ID NO: 15 or SEQ ID NO: 16, and a light chain variable region comprising the amino acid sequence as set forth in SEQ ID NO: 14. In another embodiment, the humanized monoclonal antibody or fragment thereof comprises a heavy chain variable region comprising a CDR set forth in SEQ ID NO: 15 or SEQ ID NO: 16, and a human IGHV1-3*01 framework set forth in SEQ ID NO: 18, wherein one or more of framework positions selected from the group consisting of 38, 44, and 48 are donor residues. In another embodiment, the humanized monoclonal antibody or fragment thereof comprises a light chain variable region comprising a CDR set forth in SEQ ID NO: 14 and a human IGKV3-11*01 framework set forth in SEQ ID NO: 19, wherein one or more of framework positions selected from the group consisting of 46, 70, and 71 are donor residues. In another embodiment, the humanized monoclonal antibody or fragment thereof comprises a heavy chain variable region selected from the group consisting of CDRs set forth in SEQ ID NOs: 7, 12, and 13 and a human IGH3-23 framework as set forth in SEQ ID NO: 17, wherein one or more of framework positions selected from the group consisting of 6, 18, 49, and 69 are donor residues. In another embodiment, the humanized monoclonal antibody or fragment thereof comprises a heavy chain variable region selected from the group consisting of an amino acid sequence set forth in SEQ ID NO: 7, SEQ ID NO: 12, and SEQ ID NO: 13, and a light chain variable region sequence comprising an amino acid sequence as set forth in SEQ ID NO: 14. In another embodiment, the antibody fragment is selected from the group consisting of Fab, Fab', F(ab')2, and F(v) fragments, or the individual light or heavy chain variable regions or any portion thereof.

In a particular embodiment, a kit including two or more doses of a humanized anti-αβTCR binding polypeptide and optional instructions for use is provided. In another embodiment a kit including multiple doses of a medicament comprising two or more doses of a humanized anti-αβTCR binding polypeptide, an optional pharmaceutically acceptable carrier and optional instructions for is provided. In a further embodiment, the doses are sequential doses. In a further embodiment, the instructions are for use of the kit in the any method described herein. In a further embodiment, the humanized anti-αβTCR binding polypeptide is a humanized monoclonal antibody. In a further embodiment, the humanized monoclonal antibody is GL1BM VH31, GL1BM VH28, HEBE1 H66, or HEBE1 H71. In a further embodiment, the humanized monoclonal antibody comprises a heavy chain variable region comprising the amino acid sequence set forth in SEQ ID NO: 15 or SEQ ID NO: 16, and a light chain variable region comprising the amino acid sequence as set forth in SEQ ID NO: 14. In a further embodiment, the humanized monoclonal antibody comprises a heavy chain variable region comprising a CDR set forth in SEQ ID NO: 15 or SEQ ID NO: 16, and a human IGHV1-3*01 framework set forth in SEQ ID NO: 18, wherein one or more of framework positions selected from the group consisting of 38, 44, and 48 are donor residues. In a further embodiment, the humanized monoclonal antibody comprises a light chain variable region comprising a CDR set forth in SEQ ID NO: 14 and a human IGKV3-11*01 framework set forth in SEQ ID NO: 19, wherein one or more of framework positions selected from the group consisting of 46, 70, and 71 are donor residues. In a further embodiment, the humanized monoclonal antibody comprises a heavy chain variable region selected from the group consisting of CDRs set forth in SEQ ID NOs: 7, 12, and 13 and a human IGH3-23 framework as set forth in SEQ ID NO: 17, wherein one or more of framework positions selected from the group consisting of 6, 18, 49, and 69 are donor residues. In a further embodiment, the humanized monoclonal antibody comprises a heavy chain variable region selected from the group consisting of an amino acid sequence set forth in SEQ ID NO: 7, SEQ ID NO: 12, and SEQ ID NO: 13, and a light chain variable region sequence comprising an amino acid sequence as set forth in SEQ ID NO: 14.

BRIEF DESCRIPTION OF THE FIGURES

The foregoing and other features and advantages of the present invention will be more fully understood from the following detailed description of illustrative embodiments taken in conjunction with the accompanying drawings.

FIG. 1A graphically depicts pre-apoptotic Annexin V positive αβ T cells given as a percentage of human αβ T cells. FIG. 1B graphically depicts apoptotic Annexin V and 7-AAD double positive PBMC as a percentage of all events.

FIG. 2A graphically depicts representative Annexin V and 7-AAD staining, for all time points and regimen. FIG. 2B graphically depicts the statistical evaluation of the percentage of Annexin V-positive αβ T cells after different treatments. Error bars present SEM of three independent experiments, $*=p<0.05$, $**=p<0.01$. FIG. 2C graphically depicts one of three representative experiments demonstrating the increase of γδ T cells among donor CD3+ T cells in PBMC during incubation with GZ-αβTCR. FIG. 2D graphically depicts cytokine production of IFN-γ, TNF-α, and IL-4 by αβ T cells before and after αβ-mAb treatment.

FIG. 3A schematically depicts the timeline and details of the experiment. FIG. 3B graphically depicts analyses of peripheral blood for human CD45+, CD4+, CD8+, and γδ T cells at days 0, 3, and 6 after single dose (SD) and repetitive application (RA) of GZ-αβTCR. The percentage of CD4+ and CD8+ cells among the CD3+αβ T-cells in the peripheral blood cells was set at 100% and the histogram plots show the percentage change of human CD4+ cells (upper right) and the percentage change of human CD8+ cells (lower right) as compared to the initial value at day 0 (FIG. 3B). Error bars represent SEM; d0 and d3: ■n=18, □n=17; d6 SD: ■n=9, □n=8; d6 RA: ■n=9, □n=9. $*p<0.05$; $p<0.01$; $*p<0.001$, $****p<0.0001$.

FIG. 5A schematically depicts the timeline and details of the experiment. FIG. 5B graphically depicts the analyses of peripheral blood, spleen and bone marrow (bm) for human CD3+, CD4+, CD8+ and γδ T cells at day 6. Error bars present SEM; ■n=4, □n=4. $*p<0.05$; $****p<0.0001$.

DETAILED DESCRIPTION

Figure 1A:
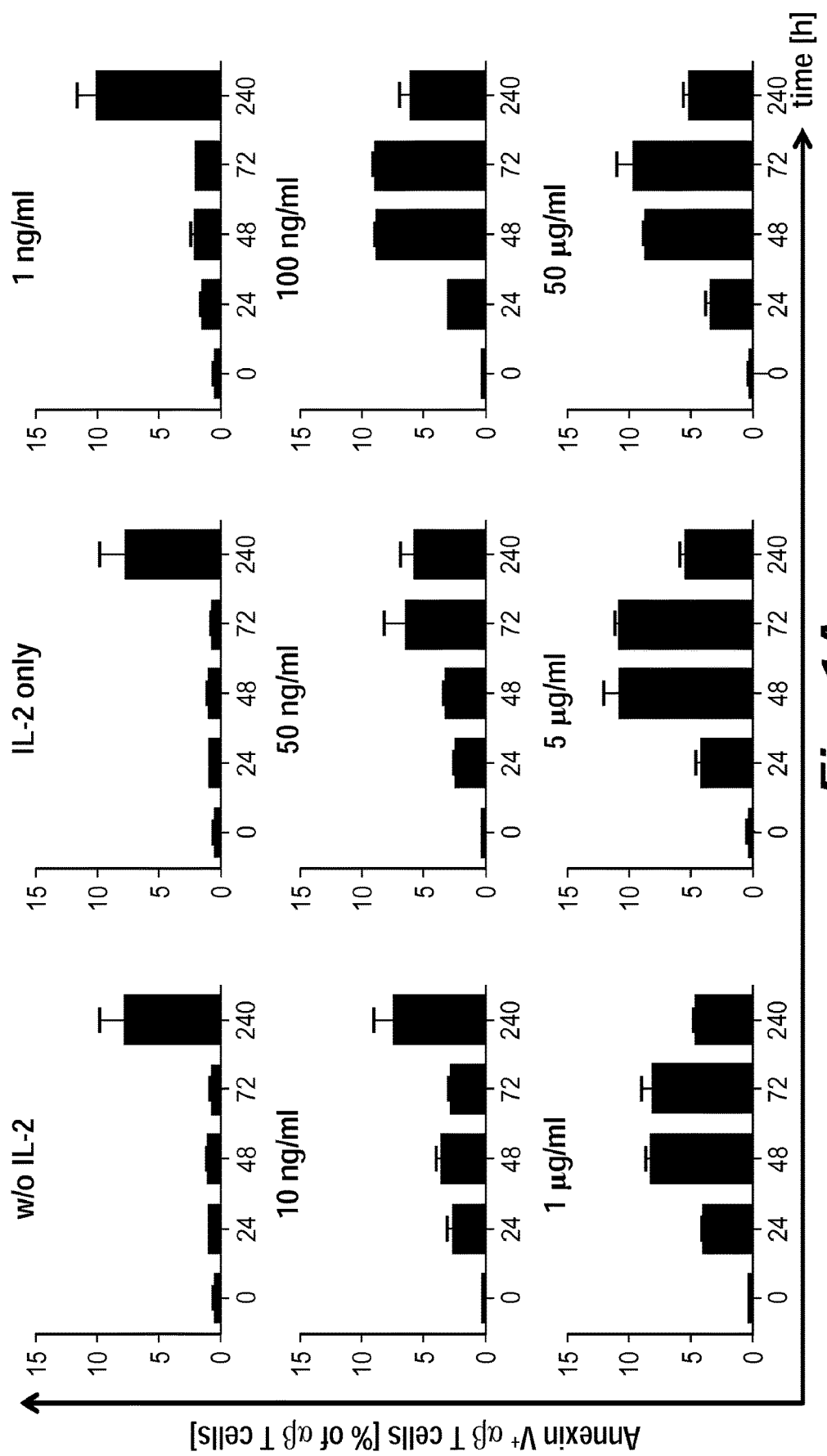
FIGS. 1A-1B graphically depict the results of flow cytometry studies demonstrating humanized αβ T-cell antibody-induced apoptosis of unstimulated αβ T cells.

The present disclosure provides improved methods for treating T cell-mediated disorders (e.g., graft-versus-host-disease and the like) in which an underlying pathology involves detrimental activation of the subject's immune system. The methods provided herein generally involve administering to a subject in need thereof an effective amount of a humanized binding polypeptide that is specific to the alpha beta T-cell receptor (αβ-TCR).

I. DEFINITIONS

Unless otherwise stated, all technical and scientific terms used herein have the same meanings as commonly understood by one of ordinary skill in the art to which this disclosure belongs. Any methods and materials similar or equivalent to those described herein can be used in the methods of techniques of the present disclosure. All publications cited herein are incorporated herein by reference in their entirety for the purpose of describing and disclosing the methodologies, reagents, and tools reported in the publications that might be used in connection with the disclosure.

The methods and techniques of the present application are generally performed according to conventional methods well known in the art and as described in various general and more specific references that are cited and discussed throughout the present specification unless otherwise indicated. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M. and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R. and Graham, A., eds. (1997) PCR (Introduction to Biotechniques Series), 2nd ed., Springer-Verlag.

The term "treatment," as used herein, refers to the care of a patient or subject with a disease, disorder and/or illness. The treatment may be directed to, but is not limited to one or any combination of the following: the cure of a disease, disorder and/or illness; the improvement of the symptoms of a disease, disorder and/or illness; and/or a prophylactic or preventative act in which the aim is to prevent or reduce the occurrence of the disease, disorder and/or illness.

The term "subject," as used herein, refers to an organism that is a vertebrate including, but not limited to: any mammal (including elephants, dogs, cats, horses, and primates such as humans, apes, or monkeys, rodents such as mice, rats, gerbils, hamsters, rabbits and/or guinea pigs and the like), birds, and/or fish.

A "humanized monoclonal antibody," as used herein, is an antibody which is composed of a human antibody framework, into which have been grafted complementarity determining regions (CDRs) from a non-human antibody. Changes in the human acceptor framework may also be made. Procedures for the design and production of humanized antibodies are well known in the art, and have been described, for example, in Cabilly et al., U.S. Pat. No. 4,816,567; Cabilly et al., European Patent Application 0 125 023; Boss et al., U.S. Pat. No. 4,816,397; Boss et al., European Patent Application 0 120 694; Neuberger, M. S. et al., WO 86/01533; Neuberger, M. S. et al., European Patent Application 0 194 276 B1; Winter, U.S. Pat. No. 5,225,539; Winter, European Patent Application 0 239 400; Padlan, E. A. et al., European Patent Application 0 519 596. Further details on antibodies, humanized antibodies, human engineered antibodies, and methods for their preparation can be found in Kontermann, R. and Dijbel, S. eds. (2001, 2010) Antibody Engineering, 2nd ed., Springer-Verlag, New York, N.Y.

The term "binding protein" or "binding polypeptide," unless indicated otherwise, is used to refer to a polypeptide (e.g., an antibody) that contains at least one binding site which is responsible for selectively binding to a target antigen of interest (e.g., a human antigen). Exemplary binding sites include an antibody variable domain, a ligand binding site of a receptor, or a receptor binding site of a ligand. In certain aspects, the binding polypeptides described herein comprise multiple (e.g., two, three, four, or more) binding sites.

The term "antibody," unless indicated otherwise, is used to refer to entire antibodies as well as antigen-binding fragments of such antibodies. For example, the term encompasses four-chain IgG molecules, as well as antibody fragments.

As used herein, the term "antibody fragment" refers to portions of an intact full-length antibody, for example, as further described below.

Antibodies may be of any class, such as IgG, IgA or IgM; and of any subclass, such as IgG1 or IgG4. Different classes and subclasses of immunoglobulin have different properties, which may be advantageous in different applications. For example, IgG4 antibodies have reduced binding to Fc receptors.

Specificity, in the context of the antibodies described herein, means that the claimed antibody is capable of selectively binding its defined cognate antigen, i.e., the αβTCR/CD3 complex. The antibodies described herein bind the αβTCR/CD3 complex expressed on cells.

The human αβTCR/CD3 complex is the T cell receptor complex presented on the surface of T cells. See, Kuhns et al. (2006) Immunity 24:133-139. This complex is targeted by the murine monoclonal antibody BMA031 (see, European patent application EP 0 403 156; SEQ ID NOs: 1 and 2, incorporated herein by reference in its entirety) and the humanized antibodies contained herein.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain (also called the $V_L$ domain) is a C-terminal portion known as the J region. Within the variable region of the heavy chain (also called the $V_H$ domain), there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3 and FR4, respectively. The locations of CDR and FR regions and a numbering system have been defined by Kabat et al. (Kabat, E. A. et al., Sequences of Proteins of Immunological Interest, Fifth Edition, U.S. Department of Health and Human Services, U.S. Government Printing Office (1991), and updates thereof which may be found online). In addition, CDR region boundaries have been further defined by IMGT nomenclature.

Variable regions of antibodies according to the described embodiments may be found in SEQ ID NOs: 5-9 and 12-16, and may be obtained by humanizing BMA031, that is, by transferring the CDRs of BMA031 to a human framework. Two series of humanized antibodies are described; the HEBE1 series, comprising SEQ ID NOs: 5-7, 12 and 13, and the GL1BM series, comprising heavy chain variable regions as shown in SEQ ID NOs: 8, 15 and 16. In both cases, the light chain variable region used is as shown in SEQ ID NO: 14 (GL1BM VK43). The human frameworks used are IGH3-23 in the case of HEBE1, and IGHV1-3*01 and IGKV3-11*01 in the case of GL1BM. Constant regions may be derived from any human antibody constant regions. Variable region genes may be cloned into expression vectors in frame with constant region genes to express heavy and light immunoglobulin chains. Such expression vectors can be transfected into antibody producing host cells for antibody synthesis.

Human antibody variable and constant regions may be derived from sequence databases. For example, immunoglobulin sequences are available in the IMGT/LIGM database (Giudicelli et al., (2006) Nucleic Acids Res. 34 (suppl. 1): D781-D784) or VBase 30 (vbase.mrc-cpe.cam.ac.uk). Aglycosylated antibodies can have extensively modified functionality; see, Boyd et al. (1996) Mol. Immunol. 32:1311-1318. A "delta ab" or Δab modification, as used herein, is an Fc modification as described in Armour et al., (1999) Eur. J. Immunol. 29:2613-2624. Techniques for modifying glycosylation of antibody Fc regions are known in the art, and include chemical, enzymatic and/or mutational means, for example, mutation of the N297 position in the CH2 domain. Techniques for mutating antibody genes for producing aglycosylated IgG molecules are described in Tao and Morrison (1989) J. Immunol. 143:2595-2601.

The term "nucleic acid," as used herein, includes DNA molecules which encode the antibodies described herein. Preferred DNA molecules which encode the antibodies described herein are expression vectors, which are suitable for expressing the antibody genes in a host cell. Expression vectors and host cells for antibody gene expression are known in the art; see, for example, Morrow, K. J. Genetic Engineering & Biotechnology News (Jun. 15, 2008) 28(12), and Backliwal, G. et al. (2008) Nucleic Acids Res. 36(15): e96-e96.

II. ANTIBODIES

This disclosure encompasses methods of administering one or more antigen-binding fragments of the humanized anti-αβTCR antibodies described herein to a subject in need thereof. Fragments of the antibodies are capable of binding the αβTCR/CD3 complex. They encompass Fab, Fab', F(ab')2, and F(v) fragments, or the individual light or heavy chain variable regions or any portion thereof. Fragments include, for example, Fab, Fab', F(ab')2, Fv, scFv and the like. In certain aspects, fragments lack the Fc portion of an intact antibody, clear more rapidly from the circulation, and/or can have less non-specific tissue binding than an intact antibody. In certain aspects, fragments can be produced from intact antibodies using well known methods, for example by proteolytic cleavage with enzymes such as papain (to produce Fab fragments) or pepsin (to produce F(ab')2 fragments).

In certain aspects, antibodies and/or antibody fragments encompass single-chain antibody fragments (scFv) that bind to the αβTCR/CD3 complex. In certain aspects, an scFv comprises an antibody heavy chain variable region (VH) operably linked to an antibody light chain variable region (VL), wherein one or both of the heavy chain variable region and the light chain variable region, together or individually, form a binding site that binds αβTCR. An scFv may comprise a VH region at the amino-terminal end and a VL region at the carboxy-terminal end. Alternatively, scFv may comprise a VL region at the amino-terminal end and a VH region at the carboxy-terminal end. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). An scFv may optionally further comprise a polypeptide linker between the heavy chain variable region and the light chain variable region.

Antibodies and antibody fragments also encompass domain antibody (dAb) fragments as described in Ward, E. S. et al. (1989) Nature 341:544-546, which consist of a VH domain. Antibodies and antibody fragments also encompass heavy chain antibodies (HCAb). HCAbs are reported to form antigen-binding regions using only heavy chain variable region, in that these functional antibodies are dimers of heavy chains only (referred to as "heavy-chain antibodies" or "HCAbs"). Accordingly, in certain aspects, antibodies and antibody fragments may be HCAbs that specifically bind to the αβTCR/CD3 complex. Antibodies and antibody fragments also encompass antibodies that are SMIPs or binding domain immunoglobulin fusion proteins specific for αβTCR/CD3 complex. These constructs are single-chain polypeptides comprising antigen-binding domains fused to immunoglobulin domains necessary to carry out antibody effector functions (see, WO 2005/017148). Antibodies and antibody fragments also encompass diabodies. Diabodies refer to bivalent antibodies in which VH and VL domains are expressed on a single polypeptide chain, but using a linker that is too short to allow for pairing between the two domains on the same chain. This forces the domains to pair with complementary domains of another chain and thereby creates two antigen-binding sites (see, for example, WO 93/11161). Diabodies can be bi-specific or mono-specific.

In certain aspects, an antibody or antibody fragment does not cross-react with any target other than the αβTCR/CD3 complex. The antibody or antibody fragment may be modified in order to increase its serum half-life, for example, by adding molecules such as PEG or other water soluble polymers, including polysaccharide polymers and the like to increase the half-life of the antibody or antibody fragment.

Antibodies and antibody fragments may be bi-specific. For example, bi-specific antibodies or antibody fragments may resemble single antibodies (or antibody fragments) that comprise two different binding sites (variable regions). Bi-specific antibodies can be produced by various methods, such as chemical techniques, "polydoma" techniques or recombinant DNA techniques. Bi-specific antibodies may have binding specificities for at least two different epitopes, at least one of which is the αβTCR/CD3 complex. The other specificity may be selected from any useful or desired specificity including, for example, specificity for human serum albumin for the extension of half-life in vivo.

The use of bi-specific antibodies in the clinic for oncology applications is now becoming reality with the tri-functional Catumaxomab (Removab®) approved for use in cases of malignant ascites and the bi-specific antibody Blinatumomab now in phase II trials in hematological malignancies. These antibodies have in common a binding arm which binds to T cells and a second arm which binds to the tumor target cell, resulting in T cell mediated lysis of the tumor target. Also in common, these molecules recruit T cells via the CD3 protein located on the cell surface. An alternative to recruitment via CD3 is to make use of the αβ T cell receptor (αβTCR), which is also expressed on the surface of the cell.

In certain exemplary embodiments, antibodies according to the present disclosure can be used to develop anti-tumor antibodies by combining a specificity for a tumor associated antigen with a specificity for the αβ T cell receptor (αβTCR).

III. ANTI-αβ-TCR ANTIBODIES

Any antibody that binds to αβTCR and inhibits or prevents a T cell-mediated disorder can be used in the methods described herein. Exemplary antibody VH, VL, and CDR amino acid sequences suitable for use as described herein are set forth in Table 1. In the sequences listed in Table 1, CDRs are indicated by means of underlining.

TABLE 1

VH, VL, and CDR amino acid sequences of exemplary anti-αβTCR antibodies.

| Antibody | Sequence | SEQ ID NO. |
|---|---|---|
| BMA031_HC_VD | EVQLQQSGPELVKPGASVKMSCKASGYKFTSYVMHWVKQKPGQGLEWI GYINPYNDVTKYNEKFKGKATLTSDKSSSTAYMELSSLTSEDSAVHYC ARGSYYDYDGFVYWGQGTLVTVSA | 1 |
| BMA031_LC_VD | QIVLTQSPAIMSASPGEKVTMTCSATSSV.SYMHWYQQKSGTSPKRWI YDTSKLASGVPARFSGSGSGTSYSLTISSMEAEDAATYYCQQWSSNPL TFGAGTKLELK | 2 |
| EuC1V3_HC_VD | QVQLVQSGAEVKKPGSSVKVSCKASGYKFTSYVMHWVKQAPGQGLEWI GYINPYNDVTKYNEKFKGKATLTADESTNTAYMELSSLRSEDTAVHYC ARGSYYDYDGFVYWGQGTLVTVSS | 3 |
| EuC1V3_LC_VD | DIQMTQSPSTLSASVGDRVTMTCSATSSV.SYMHWYQQKPGKAPKRWI YDTSKLASGVPARFIGSGSGTEFTLTISSLQPDDFATYYCQQWSSNPL TFGGGTKVEIK | 4 |
| HEBE1_HC_VD | EVQLLESGGGLVQPGGSLRLSCAASGYKFTSYVMHWVKQAPGKGLEWI GYINPYNDVTKYNEKFKGKATLSRDNSKNTLYLQMNSLRAEDTAVHYC ARGSYYDYDGFVYWGQGTLVTVSS | 5 |
| HEBE1_LC_VD | DIQMTQSPSTLSASVGDRVTMTCSATSSVSYMHWYQQKPGKAPKRWIY DTSKLASGVPARFIGSGSGTEFTLTISSLQPDDFATYYCQQWSSNPLT FGGGTKVEIK | 6 |
| HEBEI_H10_HC_VD | EVQLQQSGPELVKPGASVKMSCKAS<u>GYKFTSYVMH</u>WVKQAPGKGLEWI G<u>YINPYNDVTKYNEKFKG</u>KATLSRDNSKNTLYLQMNSLRAEDTAVHYC <u>ARGSYYDYDGFVY</u>WGQGTLVTVSS | 7 |
| GL1BM_HC_VD | QVQLVQSGAEVKKPGASVKVSCKASGYKFTSYVMHWVRQAPGQRLEWM GYINPYNDVTKYNEKFKGKATITRDTSANTAYMELSSLRSEDTAVYYC ARGSYYDYDGFVYWGQGTLVTVSS | 8 |
| GL1BM_LC_VD | EIVLTQSPATLSLSPGERATLSCSATSSVSYMHWYQQKPGQAPRRWIY DTSKLASGVPARFSGSGSGTDFTLTISSLEPEDFAVYYCQQWSSNPLT FGGGTKVEIK | 9 |
| HuIgG1 Fc delta ab | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPPVAGPSVFLFPPKPKDTLMISRTPEVTCV VVDVSHEDPEVKFNWYVDGVEVHNAKTKPREEQYNSTYRVVSVLTVLH QDWLNGKEYKCKVSNKGLPSSIEKTISKAKGQPREPQVYTLPPSRDEL TKNQVSLTCLVKGFYPSDIAVEWESNGQPENNYKTTPPVLDSDGSFFL YSKLTVDKSRWQQGNVFSCSVMHEALHNHYTQKSLSLSPGK | 10 |
| HuIgG4 agly Fc | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVDK RVESKYGPPCPPCPAPEFLGGPSVFLFPPKPKDTLMISRTPEVTCVVV DVSQEDPEVQFNWYVDGVEVHNAKTKPREEQFQSTYRVVSVLTVLHQD WLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYS RLTVDKSRWQEGNVFSCSVMHEALHNHYTQKSLSLSLGK | 11 |
| HEBEI_H66_HC_VD | EVQLLQSGGGLVQPGGSLRLSCAAS<u>GYKFTSYVMH</u>WVRQAPGKGLEWV G<u>YINPYNDVTKYNEKFKG</u>RFTLSRDNSKNTLYLQMNSLRAEDTAVYYC <u>ARGSYYDYDGFVY</u>WGQGTLVTVSS | 12 |
| HEBEI_H71_HC_VD | EVQLLESGGGLVQPGGSVRLSCAAS<u>GYKFTSYVMH</u>WVRQAPGKGLEWV G<u>YINPYNDVTKYNEKFKG</u>RFTLSRDNSKNTLYLQMNSLRAEDTAVYYC <u>ARGSYYDYDGFVY</u>WGQGTLVTVSS | 13 |

TABLE 1-continued

VH, VL, and CDR amino acid sequences of exemplary anti-αβTCR antibodies.

| Antibody | Sequence | SEQ ID NO. |
|---|---|---|
| GLBM_VK43_LC_VD | EIVLTQSPATLSLSPGERATLSC<u>SATSSVSYMH</u>WYQQKPGQAPRRLIY<br><u>DTSKLAS</u>GVPARFSGSGSGTSYTLTISSLEPEDFAVYYC<u>QQWSSNPLT</u><br>FGGGTKVEIK | 14 |
| GL1BM_VH28_HC_VD | QVQLVQSGAEVKKPGASVKVSCKAS<u>GYKFTSYVMH</u>WVKQAPGQGLEWI<br>G<u>YINPYNDVTKYNEKFKG</u>RVTITRDTSASTAYMELSSLRSEDTAVYYC<br><u>ARGSYYDYDGFVY</u>WGQGTLVTVSS | 15 |
| GL1BM_VH31_HC_VD | QVQLVQSGAEVKKPGASVKVSCKAS<u>GYKFTSYVMH</u>WVRQAPGQGLEWI<br>G<u>YINPYNDVTKYNEKFKG</u>RVTITRDTSASTAYMELSSLRSEDTAVYYC<br><u>ARGSYYDYDGFVY</u>WGQGTLVTVSS | 16 |
| IGH3-23 HEAVY CHAIN | EVQLLESGGGLVQPGGSLRLSCAAS<u>GFTFSSYAMS</u>WVRQAPGKGLEWV<br>S<u>AISGSGGSTYYADSVKG</u>RFTISRDNSKNTLYLQMNSLRAEDTAVYY<br>AK | 17 |
| IGHV1-3*01_HC | QVQLVQSGAEVKKPGASVKVSCKASGYT<u>FTSYAMH</u>WVRQAPGQRLEWM<br>G<u>WINAGNGNTKYSQKFQG</u>RVTITRDTSASTAYMELSSLRSEDTAVYYC<br>AR | 18 |
| IGKV3-11*01_LC_VD | EIVLTQSPATLSLSPGERATLSC<u>RASQSVSSYLA</u>WYQQKPGQAPRLLI<br>Y<u>DASNRAT</u>GIPARFSGSGSGTDFTLTISSLEPEDFAVYYC<u>QQRSNWP</u> | 19 |
| GL1BM VHΔS | QVQLVQSGAEVKKPGASVKVSCKASGYKFTSYVMHWVRQAPGQRLEWM<br>GYINPYNDVTKYNEKFKGKATITRDTSASTAYMELSSLRSEDTAVYYC<br>ARGSYYDYDGFVYWGQGTLVTVSS | 20 |
| GL1BM VK1 | EIVLTQSPATLSLSPGERATLSCSATSSVSYMHWYQQKPGQAPRRWIY<br>DTSKLASGVPARFSGSGSGTDFTLTISSLEPEDFAVYYCQQWSSNPLT<br>FGGGTKVEIK | 21 |
| GL1BM VK27 | EIVLTQSPATLSLSPGERATLSCSATSSVSYMHWYQQKPGQAPRRWIY<br>DTSKLASGVPARFSGSGSGTDFTLTISSMEPEDFAVYYCQQWSSNPLT<br>FGGGTKVEIK | 22 |
| GL1BM VHΔS VH11 | QVQLVQSGAEVKKPGASVKVSCKASGYKFTSYVMHWVKQKPGQGLEWI<br>GYINPYNDVTKYNEKFKGKATITRDTSASTAYMELSSLRSEDTAVYYC<br>ARGSYYDYDGFVYWGQGTLVTVSS | 23 |
| GL1BM VHΔS VH15 | QVQLVQSGAEVKKPGASVKVSCKASGYKFTSYVMHWVKQAPGQGLEWI<br>GYINPYNDVTKYNEKFKGKATITRDTSASTAYMELSSLRSEDTAVYYC<br>ARGSYYDYDGFVYWGQGTLVTVSS | 24 |

In certain embodiments, the binding polypeptide is a humanized monoclonal antibody, or a humanized monoclonal antibody fragment, comprising a heavy chain variable region selected from the heavy chains comprising the amino acid sequences set forth in SEQ ID NO: 15 and SEQ ID NO: 16, and the light chain variable region comprising the amino acid sequence as set forth in SEQ ID NO: 14.

In other embodiments, the binding polypeptide is a humanized monoclonal antibody, or a humanized monoclonal antibody fragment, comprising a heavy chain variable region comprising the CDRs set forth in SEQ ID NO: 15 and SEQ ID NO: 16, and the human IGHV1-3*01 framework set forth in SEQ ID NO: 18, wherein one or more of framework positions 38, 44, and 48 may be donor residues.

In other embodiments, the binding polypeptide is a humanized monoclonal antibody, or a humanized monoclonal antibody fragment, comprising a light chain variable region comprising the CDRs set forth in SEQ ID NO: 14 and the human IGKV3-11*01 framework set forth in SEQ ID NO: 19, wherein one or more of framework positions 46, 70, and 71 may be donor residues.

In other embodiments, the binding polypeptide is a humanized monoclonal antibody, or a humanized monoclonal antibody fragment, comprising a heavy chain variable region comprising the CDRs set forth in SEQ ID NOs: 7, 12, or 13 and the human IGH3-23 framework as set forth in SEQ ID NO: 17, wherein one or more of framework positions 6, 18, 49, and 69 may be donor residues.

In other embodiments, the binding polypeptide is a humanized monoclonal antibody, or a humanized monoclonal antibody fragment, comprising a heavy chain variable region selected from the heavy chains comprising the amino acid sequences set forth in SEQ ID NO: 7, SEQ ID NO: 12, and SEQ ID NO: 13, and the light chain variable region sequence comprising the amino acid sequence as set forth in SEQ ID NO: 14.

IV. MODIFIED ANTI-αβ-TCR ANTIBODIES

Anti-αβTCR antibodies may comprise one or more modifications. Modified anti-αβTCR antibodies according to the invention can be made using any techniques known in the art.

i) Reducing Immunogenicity

In certain exemplary embodiments, de-immunization can be used to decrease the immunogenicity of and antibody, or antigen binding portion thereof. As used herein, the term "de-immunization" includes alteration of an antibody, or antigen binding portion thereof, to modify one or more T cell epitopes (see, e.g., WO9852976A1, WO0034317A2). For example, VH and VL sequences from the starting antibody may be analyzed and a human T cell epitope "map" may be generated from each V region showing the location of epitopes in relation to complementarity-determining regions (CDRs) and other key residues within the sequence. Individual T cell epitopes from the T cell epitope map can be analyzed in order to identify alternative amino acid substitutions with a low risk of altering activity of the final antibody. A range of alternative VH and VL sequences can be designed comprising combinations of amino acid substitutions, and these sequences can be subsequently incorporated into a range of anti-αβTCR antibodies or anti-αβTCR antibody fragments for use in the methods disclosed herein, which are then tested for function. Complete heavy and light chain genes comprising modified V and human C regions can then be cloned into expression vectors and the subsequent plasmids can be introduced into cell lines for the production of whole antibody. The antibodies can then be compared in appropriate biochemical and biological assays, and the optimal variant can be identified.

ii) Effector Functions and Fc Modifications

A humanized monoclonal antibody, or a humanized monoclonal antibody fragment (e.g., an anti-αβTCR antibody or fragment thereof) may comprise an antibody constant region (e.g., an IgG constant region e.g., a human IgG constant region, e.g., a human IgG1 or IgG4 constant region) which mediates one or more effector functions. For example, binding of the C1 component of complement to an antibody constant region may activate the complement system. Activation of complement is important in the opsonisation and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. In certain embodiments, a humanized monoclonal antibody, or a humanized monoclonal antibody fragment (e.g., an anti-αβTCR antibody or fragment thereof), binds to an Fcγ receptor. In alternative embodiments, a humanized monoclonal antibody, or a humanized monoclonal antibody fragment (e.g., an anti-αβTCR antibody or fragment thereof) may comprise a constant region which is devoid of one or more effector functions (e.g., ADCC activity) and/or is unable to bind Fcγ receptor.

Certain embodiments described herein provide a humanized monoclonal antibody, or a humanized monoclonal antibody fragment (e.g., an anti-αβTCR antibody or fragment thereof) in which at least one amino acid in one or more of the constant region domains has been deleted or otherwise altered so as to provide desired biochemical characteristics such as, e.g., reduced or enhanced effector functions, the ability to non-covalently dimerize, increased ability to localize at the site of a tumor, reduced serum half-life, and/or increased serum half-life when compared with a whole, unaltered antibody of approximately the same immunogenicity. For example, certain antibodies, or fragments thereof, for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain other embodiments, a humanized monoclonal antibody, or a humanized monoclonal antibody fragment (e.g., an anti-αβTCR antibody or fragment thereof) comprises constant regions derived from different antibody isotypes (e.g., constant regions from two or more of a human IgG1, IgG2, IgG3, or IgG4). In other embodiments, a humanized monoclonal antibody, or a humanized monoclonal antibody fragment (e.g., an anti-αβTCR antibody or fragment thereof) comprises a chimeric hinge (i.e., a hinge comprising hinge portions derived from hinge domains of different antibody isotypes, e.g., an upper hinge domain from an IgG4 molecule and an IgG1 middle hinge domain).

In one embodiment, a humanized monoclonal antibody, or a humanized monoclonal antibody fragment (e.g., an anti-αβTCR antibody or fragment thereof) comprises an Fc region or portion thereof from a human IgG4 molecule and a Ser228Pro mutation (EU numbering) in the core hinge region of the molecule.

In certain exemplary embodiments, the Fc portion of a humanized monoclonal antibody, or a humanized monoclonal antibody fragment (e.g., an anti-αβTCR antibody or fragment thereof) may be mutated to increase or decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant disclosure moderate complement binding and thus reduce the serum half-life and nonspecific association of a conjugated cytotoxin. Yet other modifications of the constant region may be used to modify disulfide linkages or oligosaccharide moieties that allow for enhanced localization due to increased antigen specificity or flexibility. The resulting physiological profile, bioavailability and other biochemical effects of the modifications, such as tumor localization, bio-distribution and serum half-life, may easily be measured and quantified using well know immunological techniques without undue experimentation.

In certain embodiments, an Fc domain employed in a humanized monoclonal antibody, or a humanized monoclonal antibody fragment (e.g., an anti-αβTCR antibody or fragment thereof) is an Fc variant. As used herein, the term "Fc variant" refers to an Fc domain having at least one amino acid substitution relative to the wild-type Fc domain from which said Fc domain is derived. For example, wherein the Fc domain is derived from a human IgG1 antibody, the Fc variant of said human IgG1 Fc domain comprises at least one amino acid substitution relative to said Fc domain.

The amino acid substitution(s) of an Fc variant may be located at any position (i.e., any EU convention amino acid position) within the Fc domain. In one embodiment, the Fc variant comprises a substitution at an amino acid position located in a hinge domain or portion thereof. In another embodiment, the Fc variant comprises a substitution at an amino acid position located in a CH2 domain or portion thereof. In another embodiment, the Fc variant comprises a substitution at an amino acid position located in a CH3 domain or portion thereof. In another embodiment, the Fc variant comprises a substitution at an amino acid position located in a CH4 domain or portion thereof.

The antibodies may employ any art-recognized Fc variant which is known to impart an improvement (e.g., reduction or enhancement) in effector function and/or FcR binding. Said Fc variants may include, for example, any one of the amino acid substitutions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO05/070963A1, WO05/077981A2, WO05/092925A2, WO05/123780A2, WO06/019447A1, WO06/047350A2, and WO06/085967A2 or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784, each of which is incorporated by reference herein. In one exemplary embodiment, a humanized monoclonal antibody, or a humanized monoclonal antibody fragment (e.g., an anti-αβTCR antibody or fragment thereof) may comprise an Fc variant comprising an amino acid substitution at EU position 268 (e.g., H268D or H268E). In another exemplary embodiment, a humanized monoclonal antibody, or a humanized monoclonal antibody fragment (e.g., an anti-αβTCR antibody or fragment thereof) may comprise an amino acid substitution at EU position 239 (e.g., S239D or S239E) and/or EU position 332 (e.g., I332D or I332Q).

In certain embodiments, a humanized monoclonal antibody, or a humanized monoclonal antibody fragment (e.g., an anti-αβTCR antibody or fragment thereof) may comprise an Fc variant comprising an amino acid substitution which alters the antigen-independent effector functions of the antibody, in particular the circulating half-life of the antibody. Such antibodies exhibit either increased or decreased binding to FcRn when compared to antibodies lacking these substitutions, therefore, have an increased or decreased half-life in serum, respectively. Fc variants with improved affinity for FcRn are anticipated to have longer serum half-lives, and such molecules have useful applications in methods of treating mammals where long half-life of the administered antibody is desired, e.g., to treat a chronic disease or disorder. In contrast, Fc variants with decreased FcRn binding affinity are expected to have shorter half-lives, and such molecules are also useful, for example, for administration to a mammal where a shortened circulation time may be advantageous, e.g., for in vivo diagnostic imaging or in situations where the starting antibody has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the altered antibodies exhibit reduced transport across the epithelium of kidney glomeruli from the vasculature. In another embodiment, the altered antibodies exhibit reduced transport across the blood brain barrier (BBB) from the brain, into the vascular space. In one embodiment, an antibody with altered FcRn binding comprises an Fc domain having one or more amino acid substitutions within the "FcRn binding loop" of an Fc domain. The FcRn binding loop is comprised of amino acid residues 280-299 (according to EU numbering). Exemplary amino acid substitutions which altered FcRn binding activity are disclosed in International PCT Publication No. WO05/047327 which is incorporated by reference herein in its entirety for all purposes. In certain exemplary embodiments, a humanized monoclonal antibody, or a humanized monoclonal antibody fragment (e.g., an anti-αβTCR antibody or fragment thereof) comprises an Fc domain having one or more of the following substitutions: V284E, H285E, N286D, K290E and S304D (EU numbering).

In other embodiments, a humanized monoclonal antibody, or a humanized monoclonal antibody fragment (e.g., an anti-αβTCR antibody or fragment thereof) for use in the diagnostic and treatment methods described herein has a constant region, e.g., an IgG1 or IgG4 heavy chain constant region, which is altered to reduce or eliminate glycosylation. For example, an antibody may also comprise an Fc variant comprising an amino acid substitution which alters the glycosylation of the antibody. For example, said Fc variant may have reduced glycosylation (e.g., N- or O-linked glycosylation). In exemplary embodiments, the Fc variant comprises reduced glycosylation of the N-linked glycan normally found at amino acid position 297 (EU numbering). In another embodiment, the antibody has an amino acid substitution near or within a glycosylation motif, for example, an N-linked glycosylation motif that contains the amino acid sequence NXT or NXS. In a particular embodiment, the antibody comprises an Fc variant with an amino acid substitution at amino acid position 228 or 299 (EU numbering). In more particular embodiments, the antibody comprises an IgG1 or IgG4 constant region comprising an S228P and a T299A mutation (EU numbering).

Exemplary amino acid substitutions which confer reduced or altered glycosylation are disclosed in International PCT Publication No. WO05/018572, which is incorporated by reference herein in its entirety for all purposes. In certain embodiments, the antibodies, or fragments thereof, are modified to eliminate glycosylation. Such antibodies, or fragments thereof, may be referred to as "agly" antibodies, or fragments thereof (e.g., "agly" antibody fragments). While not intending to be bound by scientific theory, it is believed that agly antibodies, or fragments thereof, may have an improved safety and stability profile in vivo. Exemplary agly antibodies, or agly antibody fragments, comprise an aglycosylated Fc region of an IgG4 antibody which is devoid of Fc-effector function thereby eliminating the potential for Fc mediated toxicity to the normal vital organs. In yet other embodiments, agly antibodies, or agly antibody fragments, comprise an altered glycan. For example, the agly antibody or agly antibody fragment may have a reduced number of fucose residues on an N-glycan at Asn297 of the Fc region, i.e., is afucosylated. In another embodiment, the agly antibody or agly antibody fragment may have an altered number of sialic acid residues on the N-glycan at Asn297 of the Fc region.

iii) Covalent Attachment

A humanized monoclonal antibody, or a humanized monoclonal antibody fragment (e.g., an anti-αβTCR antibody or fragment thereof) may be modified, e.g., by the covalent attachment of a molecule to the antibody such that covalent attachment does not prevent the antibody from specifically binding to its cognate epitope. For example, but not by way of limitation, a humanized monoclonal antibody, or a humanized monoclonal antibody fragment (e.g., an anti-αβTCR antibody or fragment thereof), may be modified by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, and the like. Additionally, the derivative may contain one or more non-classical amino acids.

A humanized monoclonal antibody, or a humanized monoclonal antibody fragment (e.g., an anti-αβTCR antibody or fragment thereof) may further be recombinantly fused to a heterologous polypeptide at the N- or C-terminus or chemically conjugated (including covalent and non-covalent conjugations) to polypeptides or other compositions. For example, anti-αβTCR antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

A humanized monoclonal antibody, or a humanized monoclonal antibody fragment (e.g., an anti-αβTCR antibody or fragment thereof) may be fused to one or more heterologous polypeptides to increase the in vivo half-life or for use in immunoassays using methods known in the art. For example, in one embodiment, PEG can be conjugated to a humanized monoclonal antibody, or a humanized monoclonal antibody fragment (e.g., an anti-αβTCR antibody or fragment thereof) to increase its half-life in vivo. Leong, S. R., et al., Cytokine 16:106 (2001); Adv. in Drug Deliv. Rev. 54:531 (2002); or Weir et al., Biochem. Soc. Transactions 30:512 (2002).

Moreover, Aa humanized monoclonal antibody, or a humanized monoclonal antibody fragment (e.g., an anti-αβTCR antibody or fragment thereof) can be fused to one or more marker sequences, such as a peptide, to facilitate purification or detection of the humanized monoclonal antibody, or humanized monoclonal antibody fragment (e.g., an anti-αβTCR antibody or fragment thereof). In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767-778 (1984)) and the "flag" tag.

A humanized monoclonal antibody, or a humanized monoclonal antibody fragment (e.g., an anti-αβTCR antibody or fragment thereof) may be used in non-conjugated form or may be conjugated to at least one of a variety of molecules, e.g., to improve the therapeutic properties of the molecule, to facilitate target detection, or for imaging or therapy of the subject. A humanized monoclonal antibody, or a humanized monoclonal antibody fragment (e.g., an anti-αβTCR antibody or fragment thereof) can be labeled or conjugated either before or after purification, when purification is performed. In particular, a humanized monoclonal antibody, or a humanized monoclonal antibody fragment (e.g., an anti-αβTCR antibody or fragment thereof) may be conjugated to therapeutic agents, prodrugs, peptides, proteins, enzymes, viruses, lipids, biological response modifiers, pharmaceutical agents, or PEG.

The present disclosure further encompasses a humanized monoclonal antibody, or a humanized monoclonal antibody fragment (e.g., an anti-αβTCR antibody or fragment thereof) conjugated to a diagnostic or therapeutic agent. A humanized monoclonal antibody, or a humanized monoclonal antibody fragment (e.g., an anti-αβTCR antibody or fragment thereof) can be used diagnostically to, for example, monitor the development or progression of an immune cell disorder (e.g., CLL) as part of a clinical testing procedure to, e.g., determine the efficacy of a given treatment and/or prevention regimen. Detection can be facilitated by coupling a humanized monoclonal antibody, or a humanized monoclonal antibody fragment (e.g., an anti-αβTCR antibody or fragment thereof) to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present disclosure. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

A humanized monoclonal antibody, or a humanized monoclonal antibody fragment (e.g., an anti-αβTCR antibody or fragment thereof) for use in the diagnostic and treatment methods disclosed herein may be conjugated to one or more cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), or PEG.

In another embodiment, a humanized monoclonal antibody, or a humanized monoclonal antibody fragment (e.g., an anti-αβTCR antibody or fragment thereof) for use in the diagnostic and treatment methods disclosed herein can be conjugated to a molecule that decreases tumor cell growth. In other embodiments, the disclosed compositions may comprise a humanized monoclonal antibody, or a humanized monoclonal antibody fragment (e.g., an anti-αβTCR antibody or fragment thereof) coupled to drugs or prodrugs. Still other embodiments described herein comprise the use of antibodies, or fragments thereof, conjugated to specific biotoxins or their cytotoxic fragments such as ricin, gelonin, *Pseudomonas* exotoxin or diphtheria toxin or the like. The selection of which conjugated or unconjugated antibody to use will depend on the type and stage of cancer, use of adjunct treatment (e.g., chemotherapy or external radiation) and subject condition. It will be appreciated that one skilled in the art could readily make such a selection in view of the teachings herein.

It will be appreciated that, in previous studies, anti-tumor antibodies labeled with isotopes have been used successfully to destroy tumor cells in animal models, and in some cases in humans. Exemplary radioisotopes include, but are not limited to: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re. The radionuclides act by producing ionizing radiation which causes multiple strand breaks in nuclear DNA, leading to cell death. The isotopes used to produce therapeutic conjugates typically produce high energy alpha- or beta-particles which have a short path length. Such radionuclides kill cells to which they are in close proximity, for example neoplastic cells to which the conjugate has attached or has entered. They have little or no effect on non-localized cells. Radionuclides are essentially non-immunogenic.

V. ANTIBODY PRODUCTION

The amino acid sequences of the variable domains of exemplary antibodies described herein are set forth in SEQ ID NOs: 5-9 and 12-16. Antibody production can be performed by any technique known in the art, including in transgenic organisms such as goats (see, Pollock et al. (1999) J. Immunol. Methods 231:147-157), chickens (see, Morrow, K. J. J. (2000) Genet. Eng. News 20:1-55), mice (see Pollock et al., supra) or plants (see, Doran, P. M. (2000) Curr. Opinion Biotechnol. 11:199-204, Ma. J. K-C. (1998) Nat. Med. 4:601-606, Baez, J. et al. (2000) BioPharm. 13:50-54, Stoger, E. et al. (2000) Plant Mol. Biol. 42:583-590). Antibodies may also be produced by chemical synthesis or by expression of genes encoding the antibodies in host cells.

A polynucleotide encoding a humanized monoclonal antibody, or a humanized monoclonal antibody fragment (e.g., an anti-αβTCR antibody or fragment thereof) is isolated and inserted into a replicable construct or vector such as a plasmid for further propagation or expression in a host cell. Constructs or vectors (e.g., expression vectors) suitable for the expression of a humanized monoclonal antibody, or a humanized monoclonal antibody fragment (e.g., an anti-αβTCR antibody or fragment thereof) according to the described embodiments are available in the art. A variety of vectors are available, including vectors which are maintained in single copy or multiple copies in a host cell, or which become integrated into the host cell's chromosome (s). The constructs or vectors can be introduced into a suitable host cell, and cells which express a humanized immunoglobulin can be produced and maintained in culture. A single vector or multiple vectors can be used for the expression of a humanized immunoglobulin.

Polynucleotides encoding a humanized monoclonal antibody, or a humanized monoclonal antibody fragment (e.g., an anti-αβTCR antibody or fragment thereof) are readily isolated and sequenced using conventional procedures (e.g., oligonucleotide probes). Vectors that may be used include plasmid, virus, phage, transposons, minichromosomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotides encoding the light and heavy chains may be inserted into separate vectors and introduced (e.g., by transformation, transfection, electroporation or transduction) into the same host cell concurrently or sequentially or, if desired, both the heavy chain and light chain can be inserted into the same vector prior to such introduction.

A promoter can be provided for expression in a suitable host cell. Promoters can be constitutive or inducible. For example, a promoter can be operably linked to a nucleic acid encoding a humanized immunoglobulin or immunoglobulin chain, such that it directs expression of the encoded polypeptide. A variety of suitable promoters for prokaryotic and eukaryotic hosts are available. Prokaryotic promoters include lac, tac, T3, T7 promoters for E. coli; 3-phosphoglycerate kinase or other glycolytic enzymes e.g., enolase, glyceralderhyde 3-phosphate dehydrogenase, hexokinase, pyruvate decarboxylase, phosphofructokinase, glucose 6 phosphate isomerase, 3-phosphoglycerate mutase and glucokinase. Eukaryotic promoters include inducible yeast promoters such as alcohol dehydrogenase 2, isocytochrome C, acid phosphatase, metallothionein and enzymes responsible for nitrogen metabolism or maltose/galactose utilization; RNA polymerase II promoters including viral promoters such as polyoma, fowlpox and adenoviruses (e.g., adenovirus 2), bovine papilloma virus, avian sarcoma virus, cytomegalovirus (in particular, the immediate early gene promoter), retrovirus, hepatitis B virus, actin, rous sarcoma virus (RSV) promoter and the early or late Simian virus 40 and non-viral promoters such as EF-1 alpha (Mizushima and Nagata (1990) Nucleic Acids Res. 18(17):5322). Those of skill in the art will be able to select the appropriate promoter for expressing a humanized antibody or portion thereof.

Where appropriate, e.g., for expression in cells of higher eukaroytes, additional enhancer elements can be included instead of or as well as those found located in the promoters described above. Suitable mammalian enhancer sequences include enhancer elements from globin, elastase, albumin, fetoprotein, metallothionine and insulin. Alternatively, one may use an enhancer element from a eukaryotic cell virus such as SV40 enhancer, cytomegalovirus early promoter enhancer, polyoma enhancer, baculoviral enhancer or murine IgG2a locus (see, WO 04/009823). Whilst such enhancers are often located on the vector at a site upstream to the promoter, they can also be located elsewhere e.g., within the untranslated region or downstream of the polyadenylation signal. The choice and positioning of enhancer may be based upon compatibility with the host cell used for expression.

In addition, the vectors (e.g., expression vectors) may comprise a selectable marker for selection of host cells carrying the vector, and, in the case of a replicable vector, an origin of replication. Genes encoding products which confer antibiotic or drug resistance are common selectable markers and may be used in prokaryotic (e.g., f3-lactamase gene (ampicillin resistance), tet gene (tetracycline resistance) and eukaryotic cells (e.g., neomycin (G418 or geneticin), gpt (mycophenolic acid), ampicillin, or hygromycin 5 resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

In eukaryotic systems, polyadenylation and termination signals are operably linked to polynucleotide encoding the antibody described herein. Such signals are typically placed 3' of the open reading frame. In mammalian systems, non-limiting examples of polyadenylation/termination signals include those derived from growth hormones, elongation factor-1 alpha and viral (e.g., SV40) genes or retroviral long terminal repeats. In yeast systems, non-limiting examples of polydenylation/termination signals include those derived from the phosphoglycerate kinase (PGI) and the alcohol dehydrogenase 1 (ADH) genes. In prokaryotic systems polyadenylation signals are typically not required and it is instead usual to employ shorter and more defined terminator sequences. The choice of polyadenylation/termination sequences may be based upon compatibility with the host cell used for expression. In addition to the above, other features that can be employed to enhance yields include chromatin remodeling elements, introns and host cell specific codon modification. The codon usage of the antibodies described herein can be modified to accommodate codon bias of the host cell such to augment transcript and/or product yield (e.g., Hoekema, A. et al. (1987) MoL Cell Biol. 7(8):2914-24). The choice of codons may be based upon compatibility with the host cell used for expression.

This disclosure thus relates to isolated nucleic acid molecules that encode the humanized immunoglobulins, or heavy or light chains, thereof. This disclosure also relates to isolated nucleic acid molecules that encode an antigen-binding portion of the immunoglobulins and their chains.

A humanized monoclonal antibody, or a humanized monoclonal antibody fragment (e.g., an anti-αβTCR antibody or fragment thereof) can be produced, for example, by the expression of one or more recombinant nucleic acids encoding the antibody in a suitable host cell. The host cell can be produced using any suitable method. For example, the expression constructs (e.g., one or more vectors, e.g., a mammalian cell expression vector) described herein can be introduced into a suitable host cell, and the resulting cell can be maintained (e.g., in culture, in an animal, in a plant) under conditions suitable for expression of the construct(s) or vector(s). Host cells can be prokaryotic, including bacterial cells such as E. coli (e.g., strain DH5aTM) (Invitrogen, Carlsbad, Calif.), PerC6 (Crucell, Leiden, NL), B. subtilis and/or other suitable bacteria; eukaryotic cells, such as fungal or yeast cells (e.g., Pichia pastoris, Aspergillus sp., Saccharomyces cerevisiae, Schizosaccharomyces pombe, Neurospora crassa), or other lower eukaryotic cells, and cells of higher eukaryotes such as those from insects (e.g., Drosophila Schnieder S2 cells, Sf9 insect cells) (WO 94/126087 (O'Connor)), BTI-TN-5B1-4 (High Five™) insect cells (Invitrogen), mammals (e.g., COS cells, such as COS-1 (ATCC Accession No. CRL-1650) and COS-7 (ATCC Accession No. CRL-1651), CHO (e.g., ATCC Accession No. CRL-9096), CHO DG44 (Urlaub, G. and Chasin, L. A. (1980) Proc. Natl. Acad. Sci. USA, 77(7): 4216-4220), 293 (ATCC Accession No. CRL-1573), HeLa (ATCC Accession No. CCL-2), CVI (ATCC Accession No. CCL-70), WOP (Dailey, L., et al. (1985) J. Viol., 54:739-749), 3T3, 293T (Pear, W. S., et al. (1993) Proc. Natl. Acad. Sci. U.S.A., 90:8392-8396), NSO cells, SP2/0 cells, HuT 78 cells, and the like, or plants (e.g., tobacco, lemna (duckweed), and algae). See, for example, Ausubel, F. M. et al., eds. Current Protocols in Molecular Biology, Greene Publishing Associates and John Wiley & Sons Inc. (1993). In some embodiments, the host cell is not part of a multicellular organism (e.g., plant or animal), e.g., it is an isolated host cell or is part of a cell culture.

Host cells may be cultured in spinner flasks, shake flasks, roller bottles, wave reactors (e.g., System 1000 from wavebiotech.com) or hollow fiber systems but it is preferred for large scale production that stirred tank reactors or bag reactors (e.g., Wave Biotech, Somerset, N.J. USA) are used particularly for suspension cultures. Stirred tank reactors can be adapted for aeration using e.g., spargers, baffles or low shear impellers. For bubble columns and airlift reactors, direct aeration with air or oxygen bubbles maybe used. Where the host cells are cultured in a serum-free culture medium, the medium can be supplemented with a cell protective agent such as pluronic F-68 to help prevent cell damage as a result of the aeration process. Depending on the host cell characteristics, microcarriers may be used as growth substrates for anchorage dependent cell lines, or the cells may be adapted to suspension culture. The culturing of host cells, particularly vertebrate host cells, may utilize a variety of operational modes such as batch, fed-batch, repeated batch processing (see, Drapeau et al. (1994) Cytotechnology 15:103-109), extended batch process or perfusion culture. Although recombinantly transformed mammalian host cells may be cultured in serum-containing media such media comprising fetal calf serum (FCS), it is preferred that such host cells are cultured in serum-free media such as disclosed in Keen et al. (1995) Cytotechnology 17:153-163, or commercially available media such as ProCHO-CDM or UltraCHOTM (Cambrex N.J., USA), supplemented where necessary with an energy source such as glucose and synthetic growth factors such as recombinant insulin. The serum-free culturing of host cells may require that those cells are adapted to grow in serum-free conditions. One adaptation approach is to culture such host cells in serum containing media and repeatedly exchange 80% of the culture medium for the serum-free media so that the host cells learn to adapt in serum-free conditions (see, e.g., Scharfenberg, K. et al. (1995) Animal Cell Technology: Developments Towards the 21st Century (Beuvery, E. C. et al., eds), pp. 619-623, Kluwer Academic publishers).

A humanized monoclonal antibody, or a humanized monoclonal antibody fragment (e.g., an anti-αβTCR antibody or fragment thereof) according to the described embodiments may be secreted into the medium and recovered and purified therefrom using a variety of techniques to provide a degree of purification suitable for the intended use. For example, the use of a humanized monoclonal antibody, or a humanized monoclonal antibody fragment (e.g., an anti-αβTCR antibody or fragment thereof) for the treatment of human subjects typically mandates at least 95% purity as determined by reducing SDS-PAGE, more typically 98% or 99% purity, when compared to the culture media comprising the therapeutic antibodies. In the first instance, cell debris from the culture media can be removed using centrifugation followed by a clarification step of the supernatant using e.g., microfiltration, ultrafiltration and/or depth filtration. Alternatively, a humanized monoclonal antibody, or a humanized monoclonal antibody fragment (e.g., an anti-αβTCR antibody or fragment thereof) can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC) (see, U.S. Pat. No. 5,429,746) are available. In one embodiment, a humanized monoclonal antibody, or a humanized monoclonal antibody fragment (e.g., an anti-αβTCR antibody or fragment thereof), following various clarification steps, are captured using Protein A or G affinity chromatography followed by further chromatography steps such as ion exchange and/or HA chromatography, anion or cation exchange, size exclusion chromatography and ammonium sulphate precipitation. Various virus removal steps may also be employed (e.g., nanofiltration using, e.g., a DV-20 filter). Following these various steps, a purified preparation comprising at least 10 mg/ml or greater, e.g., 100 mg/ml or greater of the antibody described herein is provided and, therefore, forms another embodiment described herein. Concentration to 100 mg/ml or greater can be generated by ultracentrifugation. Such preparations are substantially free of aggregated forms of antibodies described herein.

Bacterial systems are particularly suited for the expression of antibody fragments. Such fragments are localized intracellularly or within the periplasm. Insoluble periplasmic proteins can be extracted and refolded to form active proteins according to methods known to those skilled in the art, see, Sanchez et al. (1999) J. Biotechnol. 72:13-20; Cupit, P. M. et al. (1999) Lett. Appl. Microbiol. 29:273-277.

The present disclosure also relates to cells comprising a nucleic acid, e.g., a vector, described herein (e.g., an expression vector). For example, a nucleic acid (i.e., one or more nucleic acids) encoding the heavy and light chains of a humanized immunoglobulin according to the described embodiments, or a construct (e.g., one or more constructs, e.g., one or more vectors) comprising such nucleic acid(s), can be introduced into a suitable host cell by a method appropriate to the host cell selected (e.g., transformation, transfection, electroporation, infection), with the nucleic acid(s) being, or becoming, operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded humanized antibody can be isolated, for example, from the host cells, culture medium, or milk. This process encompasses expression in a host cell (e.g., a mammary gland cell) of a transgenic animal or plant (e.g., tobacco) (see, e.g., WO 92/03918).

VI. PHARMACEUTICAL COMPOSITIONS AND METHODS OF ADMINISTRATION OF ANTI-αβ-TCR ANTIBODIES

In certain embodiments, pharmaceutical compositions comprising a humanized monoclonal antibody, or a humanized monoclonal antibody fragment (e.g., an anti-αβTCR antibody or fragment thereof) described herein, or a ligand or ligands identifiable by an assay method as defined in the previous aspect of the disclosure are provided. Ligands may be immunoglobulins, peptides, nucleic acids or small molecules, as discussed herein. They are referred to, in the following discussion, as "compounds."

A pharmaceutical composition described herein is a composition of matter comprising a compound or compounds capable of modulating T cell activity as an active ingredient. The compound is in the form of any pharmaceutically acceptable salt, or e.g., where appropriate, is an analog, free base form, tautomer, enantiomer racemate, or combination thereof. The active ingredients of a pharmaceutical composition comprising the active ingredient described herein are contemplated to exhibit therapeutic activity, for example, in the treatment of graft-versus-host disease, when administered in an amount which depends on the particular case.

In another embodiment, one or more compounds described in this disclosure may be used in combination with any art recognized compound known to be suitable for treating the particular indication in treating any of the aforementioned conditions. Accordingly, one or more compounds described herein may be combined with one or more art recognized compounds known to be suitable for treating the foregoing indications such that a convenient, single composition can be administered to the subject. Dosage regimes may be adjusted to provide the optimum therapeutic response.

For example, several divided doses may be administered daily or the dose may be proportionally reduced as indicated by the exigencies of the therapeutic situation.

The active ingredient may be administered in a convenient manner such as by the oral, intravenous (where water soluble), intramuscular, subcutaneous, intranasal, intradermal or suppository routes or implanting (e.g., using slow release molecules). In the case of a transplant, the active ingredient may also be used to treat cells, tissues, or organs being transplanted into a patient prior to the transplantation. This may be done in order to prevent, decrease the likelihood, or lessen the symptoms of, for example, graft versus host disease.

Depending on the route of administration, the active ingredient may be required to be coated in a material to protect said ingredients from the action of enzymes, acids and other natural conditions which may inactivate said ingredient.

In order to administer the active ingredient by means other than parenteral administration, it will be coated by, or administered with, a material to prevent its inactivation. For example, the active ingredient may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin.

Liposomes include water-in-oil-in-water CGF emulsions as well as conventional liposomes.

The active ingredient may also be administered parenterally or intraperitoneally.

Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thirmerosal, and the like. In certain cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredient in the required amount in the appropriate solvent with several of the other ingredients enumerated above, as required, followed by filtered sterilization.

Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Various other materials may be present as coatings or to otherwise modify the physical form of the dosage unit. Of course, any material used in preparing any dosage unit form should be pharmaceutically pure and substantially non-toxic in the amounts employed. In addition, the active ingredient may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms described herein are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired. The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

Dosages may include, but are not limited to, 0.01 mg/kg to 20 mg/kg, including: 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.10 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.00 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10.0 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11.0 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12.0 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, 13.0 mg/kg, 13.1 mg/kg, 13.2 mg/kg, 13.3 mg/kg, 13.4 mg/kg, 13.5 mg/kg, 13.6 mg/kg, 13.7 mg/kg, 13.8 mg/kg, 13.9 mg/kg, 14.0 mg/kg, 14.1 mg/kg, 14.2 mg/kg, 14.3 mg/kg, 14.4 mg/kg, 14.5 mg/kg, 14.6 mg/kg, 14.7 mg/kg, 14.8 mg/kg, 14.9 mg/kg, 15.0 mg/kg, 15.1 mg/kg, 15.2 mg/kg, 15.3 mg/kg, 15.4 mg/kg, 15.5 mg/kg, 15.6 mg/kg, 15.7 mg/kg, 15.8 mg/kg, 15.9 mg/kg, 16.0 mg/kg, 16.1 mg/kg, 16.2 mg/kg, 16.3 mg/kg, 16.4 mg/kg, 16.5 mg/kg, 16.6 mg/kg, 16.7 mg/kg, 16.8 mg/kg, 16.9 mg/kg, 17.0 mg/kg, 17.1 mg/kg, 17.2 mg/kg, 17.3 mg/kg, 17.4 mg/kg, 17.5 mg/kg, 17.6 mg/kg, 17.7 mg/kg, 17.8 mg/kg, 17.9 mg/kg, 18.0 mg/kg, 18.1 mg/kg, 18.2 mg/kg, 18.3 mg/kg, 18.4 mg/kg, 18.5 mg/kg, 18.6 mg/kg, 18.7 mg/kg, 18.8 mg/kg, 18.9 mg/kg, 19.0 mg/kg, 19.1 mg/kg, 19.2 mg/kg, 19.3 mg/kg, 19.4 mg/kg, 19.5 mg/kg, 19.6 mg/kg, 19.7 mg/kg, 19.8 mg/kg, 19.9 mg/kg, and 20.0 mg/kg.

Dosages may also include, but are not limited to: about 100 ng/kg to about 0.01 mg/kg, including: about 100 ng/kg, about 200 ng/kg, about 300 ng/kg, about 400 ng/kg, about 500 ng/kg, about 600 ng/kg, about 700 ng/kg, about 800 ng/kg, about 900 ng/kg, about 1 microgram/kg, about 2 microgram/kg, about 3 microgram/kg, about 4 microgram/kg, about 5 microgram/kg, about 6 microgram/kg, about 7 microgram/kg, about 8 microgram/kg, about 9 microgram/kg, about 10 microgram/kg.

In order to facilitate delivery of peptide compounds, including antibodies, to cells, peptides may be modified in order to improve their ability to cross a cell membrane. For example, U.S. Pat. No. 5,149,782 discloses the use of fusogenic peptides, ion-channel forming peptides, membrane peptides, long-chain fatty acids and other membrane blending agents to increase protein transport across the cell membrane. These and other methods are also described in WO 97/37016 and U.S. Pat. No. 5,108,921, incorporated herein by reference.

In a further aspect there is provided the active ingredient described herein for use in the treatment of disease either alone or in combination with art recognized compounds known to be suitable for treating the particular indication. Consequently there is provided the use of an active ingredient described herein for the manufacture of a medicament for the treatment of disease associated with an aberrant immune response.

Moreover, there is provided a method for treating a condition associated with an aberrant immune response, comprising administering to a subject a therapeutically effective amount of a ligand identifiable using an assay method as described above.

VIII. METHODS OF TREATING OR PREVENTING T CELL-MEDIATED DISORDERS

Suppression of T cell activity is desirable in a number of situations in which immunosuppression is warranted, and/or an autoimmune condition occurs. Accordingly, targeting of the αβTCR/CD3 complex is indicated in the treatment of diseases involving an inappropriate or undesired immune response, such as inflammation, autoimmunity, and/or other conditions involving such mechanisms. In one embodiment, such disease or disorder is an autoimmune and/or inflammatory disease. Examples of such autoimmune and/or inflammatory T-cell mediated diseases include but are not limited to: systemic lupus erythematosus (SLE), rheumatoid arthritis (RA) and inflammatory bowel disease (IBD) (including ulcerative colitis (UC) and Crohn's disease (CD)), multiple sclerosis (MS), scleroderma and type 1 diabetes (T1D), and other diseases and disorders, such as pemphigus vulgaris (PV), psoriasis, atopic dermatitis, celiac disease, chronic obstructive lung disease, Hashimoto's thyroiditis, Graves' disease (thyroid), Sjogren's syndrome, Guillain-Barre syndrome, Goodpasture's syndrome, Addison's disease, Wegener's granulomatosis, primary biliary sclerosis, sclerosing cholangitis, autoimmune hepatitis, polymyalgia rheumatica, Raynaud's phenomenon, temporal arteritis, giant cell arteritis, autoimmune hemolytic anemia, pernicious anemia, polyarteritis nodosa, behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia areata, and vitilgo.

In one embodiment, such disease or disorder is SLE, RA or IBD. In one embodiment, such disease or disorder is MS.

In another embodiment, such disease or disorder is a xenotransplant, an allotransplant, a xenopregnancy, pre-eclampsia, or Rh disease.

In another embodiment, such disease is systemic lupus erythematosus (SLE), rheumatoid arthritis (RA) and inflammatory bowel disease (IBD) (including ulcerative colitis (UC) and Crohn's disease (CD)), multiple sclerosis (MS), scleroderma and type 1 diabetes (T1D), and other diseases and disorders, such as pemphigus vulgaris (PV), psoriasis, atopic dermatitis, celiac disease, chronic obstructive lung disease, Hashimoto's thyroiditis, Graves' disease (thyroid), Sjogren's syndrome, Guillain-Barre syndrome, Goodpasture's syndrome, Addison's disease, Wegener's granulomatosis, primary biliary sclerosis, sclerosing cholangitis, autoimmune hepatitis, polymyalgia rheumatica, Raynaud's phenomenon, temporal arteritis, giant cell arteritis, autoimmune hemolytic anemia, pernicious anemia, polyarteritis nodosa, behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia areata, or vitilgo.

In specific embodiments, the antibodies according to the described embodiments are used to aid transplantation by immuno suppressing the subject. Such use alleviates graft-versus-host disease (GVHD), a common complication following xenograft or allograft (including, but not limited to: the transplant of stem cells, bone marrow, tissues, body parts, and solid organs). Tissues may include, but are not limited to: cornea, sclera, bone, skin, blood vessels, and heart valves. Body parts may include, but are not limited to: a face or a portion thereof, one or more arms or portions thereof, one or more hands or portions thereof, one or more legs or portions thereof, and a scalp or portions thereof. Solid organs may include, but are not limited to: heart, lung, liver, kidney, pancreas, stomach, small intestine, large intestine, testis and ovary. For a description of existing treatments for graft-versus-host disease, see, e.g., Svennilson, Bone Marrow Transplantation (2005) 35:S65-S67, and references cited therein. Advantageously, the antibodies presented in this disclosure may be used in combination with other available therapies.

With regard to the treatment of autoimmune diseases, combination therapy may include administration of an antibody described herein together with a medicament, which together with the antibody comprises an effective amount for preventing or treating such autoimmune diseases. Where said autoimmune disease is Type 1 diabetes, the combination therapy may encompass one or more of an agent that promotes the growth of pancreatic beta-cells or enhances beta-cell transplantation, such as beta cell growth or survival factors or immunomodulatory antibodies. Where said autoimmune disease is rheumatoid arthritis, said combination therapy may encompass one or more of methotrexate, an anti-TNF-p antibody, a TNF-p receptor-Ig fusion protein, an anti-IL-15 or anti-IL-21 antibody, a non-steroidal anti-inflammatory drug (NSAID), or a disease-modifying anti-rheumatic drug (DMARD). For example, the additional agent may be a biological agent such as an anti-TNF agent (e.g., ENBREL®, infliximab (REMICADE®) and adalimumab (HUMIRA®) or rituximab (RITUXAN®). Where said autoimmune disease is hematopoietic transplant rejection, hematopoietic growth factor(s) (such as erythropoietin, G-CSF, GM-CSF, IL-3, IL-11, thrombopoietin, etc.) or antimicrobial(s) (such as antibiotic, antiviral, antifungal drugs) may be administered. Where said autoimmune disease is psoriasis, the additional agent may be one or more of tar and derivatives thereof, phototherapy, corticosteroids, cyclosporine A, vitamin D analogs, methotrexate, p38 mitogen-activated protein kinase (MAPK) inhibitors, as well as biologic agents such as anti-TNF-agents and RITUXAN®. Where said autoimmune disease is an inflammatory bowel disease (IBD) such as, for example, Crohn's Disease or ulcerative colitis, the additional agent may be one or more of aminosalicylates, corticosteroids, immunomodulators, antibiotics, or biologic agents such as REMICADE® and HUMIRA®.

The combination treatment may be carried out in any way as deemed necessary or convenient by the person skilled in the art and for the purpose of this specification, no limitations with regard to the order, amount, repetition or relative amount of the compounds to be used in combination is contemplated. Accordingly, the antibodies according to the described embodiments may be formulated into pharmaceutical compositions for use in therapy.

The examples provided below are for the purposes of illustration only, and should not be considered limiting on the compositions and methods described herein.

IX. EXEMPLIFICATION

Human peripheral blood mononuclear cells (hPBMC) were obtained from healthy adult volunteers and blood donors, under signed informed consent in accordance with the declaration of Helsinki. hPBMC were collected in heparin, isolated and purified by Ficoll density-gradient centrifugation (PAA Laboratories, Germany).

Example 1: Antibodies that Target αβTCR Induced Apoptosis In Vitro

The humanized αβ T-cell antibody (αβ mAb) GZ αβTCR was tested for its ability to induce apoptosis in T cells in human peripheral blood mononuclear cell (hPBMC cultures).

hPBMCs were obtained from healthy adult volunteers and blood donors under signed informed consent in accordance with the declaration of Helsinki. The hPBMC were collected in heparin, isolated, and purified by Ficoll density-gradient centrifugation (PAA Laboratories, Germany).

2×10$^5$ hPBMCs were incubated for up to 48 hours with low dose IL-2 (30 U/mL). Further treatment was as indicated (60Gy-irradiation, incubation with isotype mAbs or GZ αβTCR [100 ng/mL]). Thereafter, cells were washed and stained with fluorescence-labeled mAbs and analysed using a FACS Calibur flow cytometer.

Figure 1B:
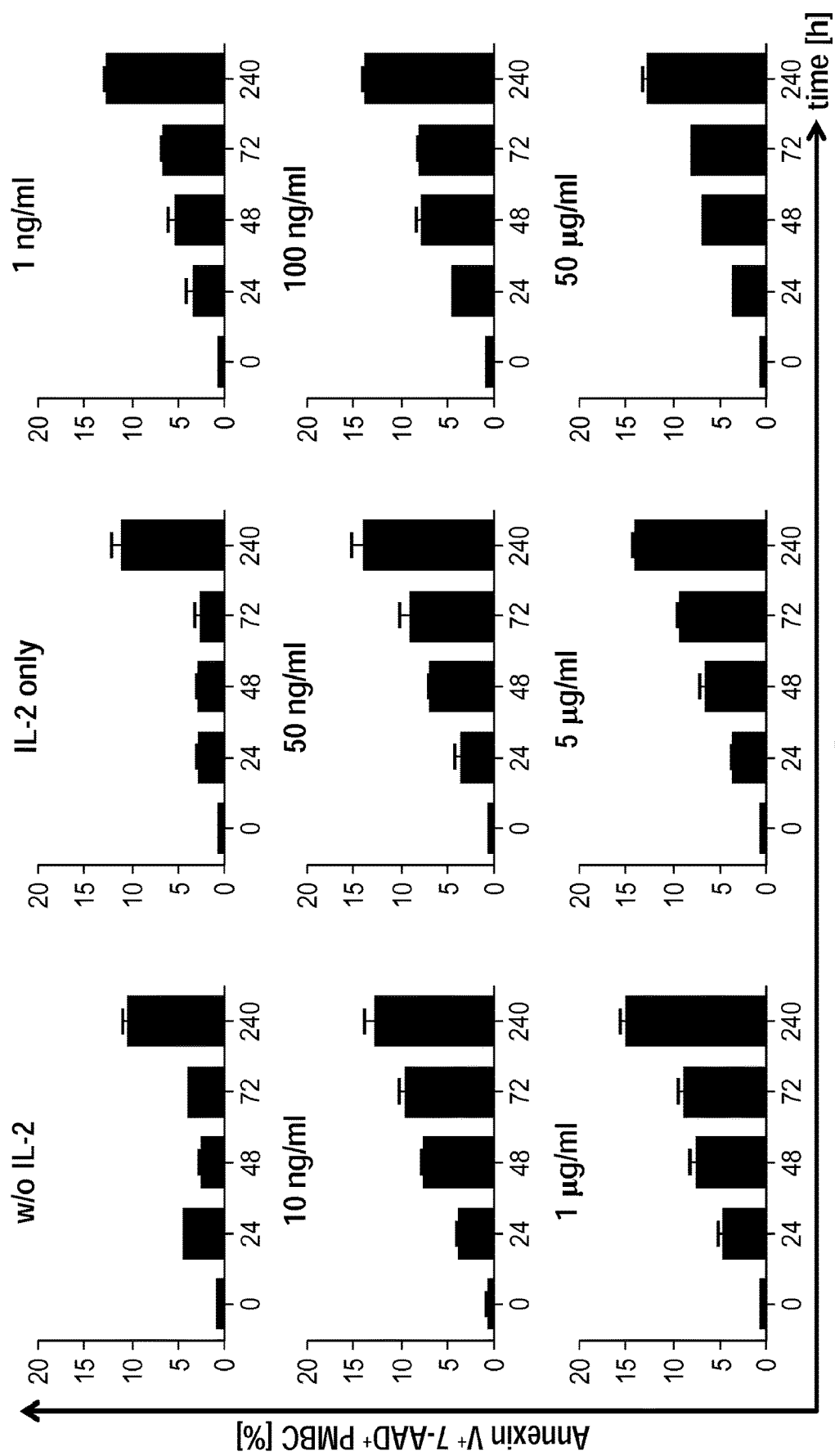

Incubation with GZ αβTCR steadily increased the proportion of Annexin V+αβ T cells in all cultures over time (FIGS. 1A-B). An up to five-fold increase in the proportion of Annexin V+αβ T cells was observed after 48 h compared to control. Concomitantly, a continuous increase of apoptotic Annexin V and 7-AAD double positive cells was observed (FIG. 1B). Induction of apoptosis was both time- and dose-dependent. Maximum efficacy was observed at doses of no less than 100 ng/mL and after 48 hours of incubation. The maximum of αβ T cells positive for Annexin V after 48 h in vitro was about 10%. Induction of apoptosis was both time- and dose-dependent. Maximum efficacy was observed at doses ≥100 ng/mL and after 48 hours of incubation.

Example 2: αβ T-Cell Antibodies were Potent Inducers of Apoptosis in Activated αβ T-Cells hPBMC were suspended at a concentration of 1×10$^6$ cells/ml in RPMI 1640-medium supplemented with 10% heat-inactivated FCS (Biochrom, Germany), L-Glutamine (4 mM), and Penicillin (50 U/ml)/Streptomycin (50 μg/ml) and plated in 96-well U-bottom microtiter plates (Costar, USA). Plates were incubated at 37° C., 5% CO2, 95% humidity.

In order to test the efficacy of αβ mAb treatment to induce apoptosis in activated hPBMC, 2×10$^5$ PBMCs were stimulated with anti-CD3/CD28 beads (Dynabeads® Human T-Activator CD3/CD28) for 24 hours in a 1:1 bead-to-cell ratio according to the manufacturer's protocol (Invitrogen, Darmstadt, Germany). Following an initial 24 hour incubation, 100 ng/mL GZ αβTCR was added to the culture and the cells were subsequently incubated for a further 48 hours.

Detection of apoptosis was performed using the PE-Annexin V Apoptosis Detection Kit I (BD Biosciences, Germany) according to the manufacturer's protocol. Representative Annexin V and 7-AAD staining of αβ T cells are shown for all time points and treatments (FIG. 2A).

Figure 2A:
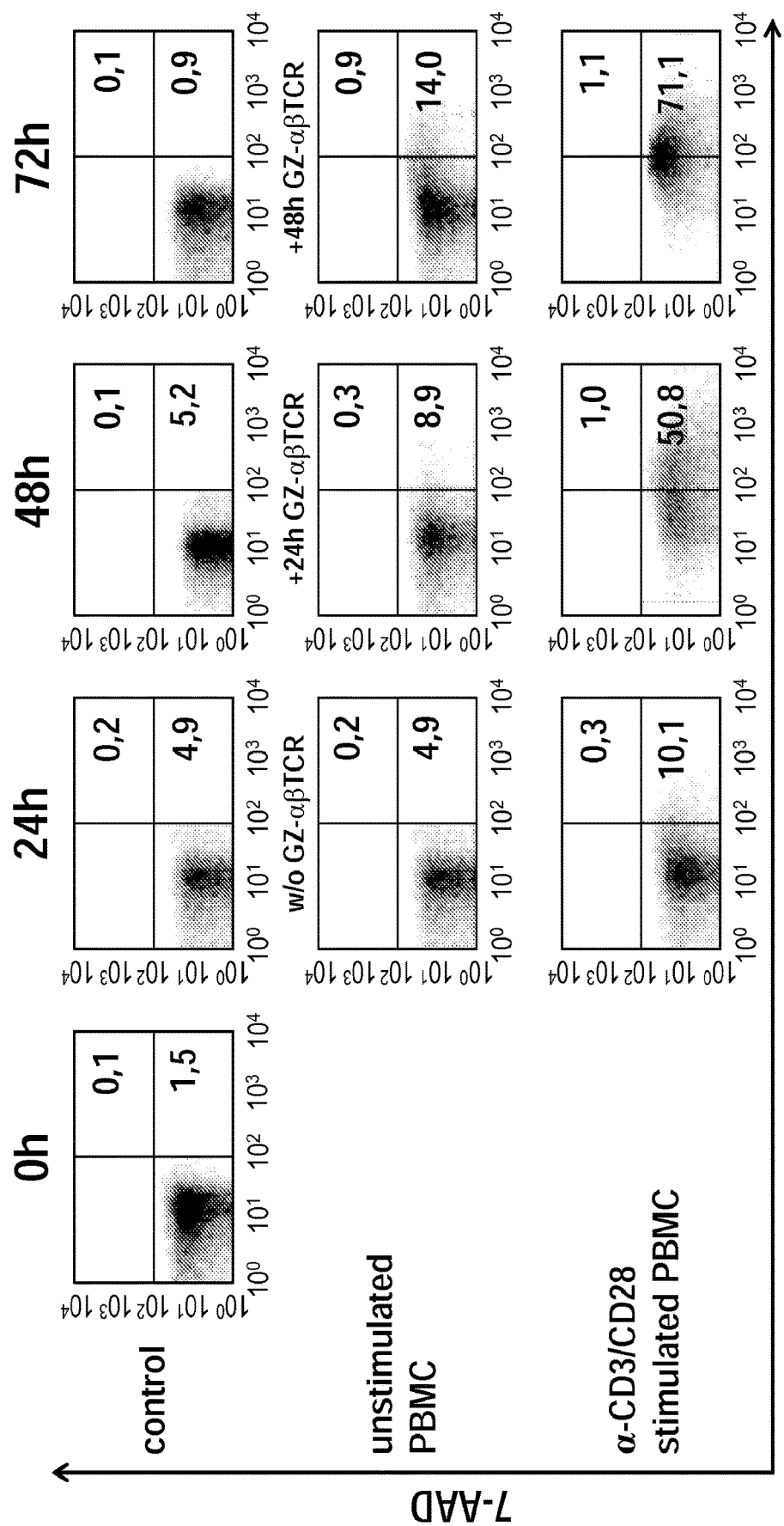
FIGS. 2A-2D graphically depict the results of flow cytometry studies demonstrating humanized αβ T-cell antibody-induced apoptosis of activated αβ T cells.
Figure 2B:
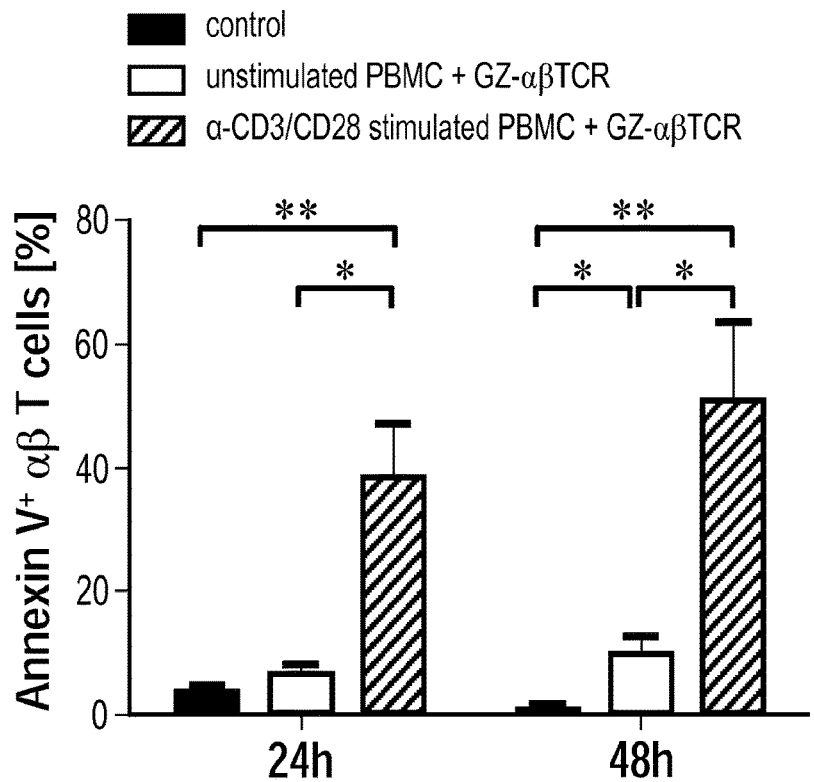

Preactivation of T cells raised the percentage of Annexin V+αβ T cells to 50.90% (+/−12.50%) after incubation with the GZ-αβTCR antibody for 48 h (as compared to less than 2% in unstimulated control hPBMC) (FIG. 2A, FIG. 2B). Error bars present SEM of four independent experiments (*P<0.05; **P<0.01 using the unpaired two-tailed t-test and GraphPad Prism software (Graphpad Software, USA)).

Figure 2C:
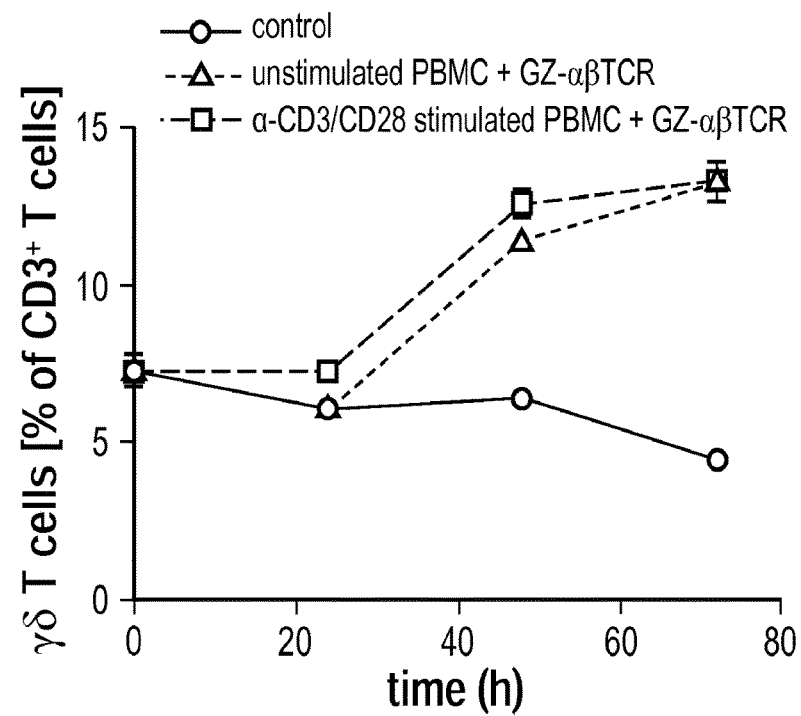

While the proportion of αβ T cells in culture decreased due to the demonstrated apoptosis, γδ T cells were mostly unaffected, raising their proportion in the culture during incubation with GZ-αβTCR (FIG. 2C).

Figure 2D:
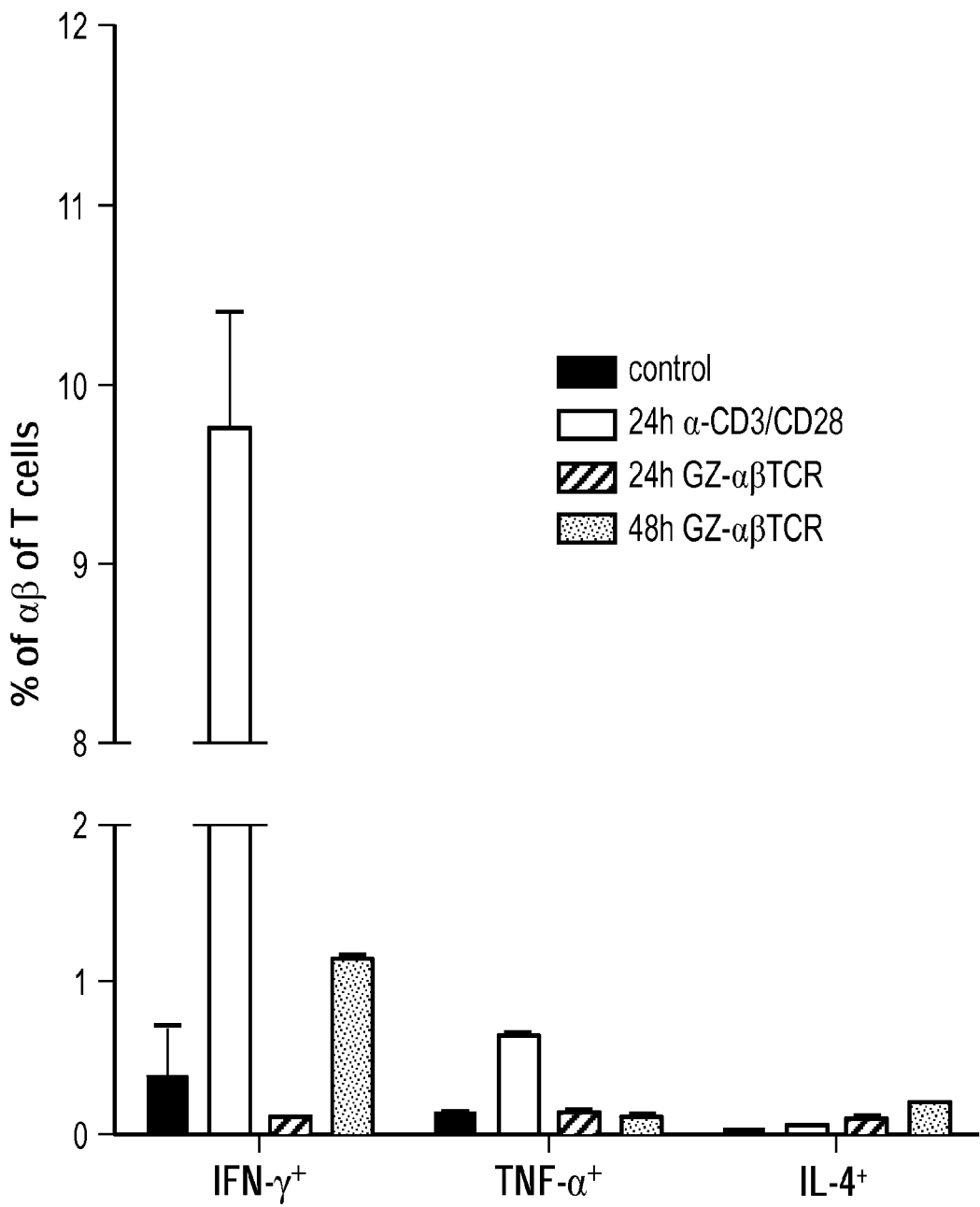

Intracellular FACS-stainings demonstrate that the induction of apoptosis in αβ T-cells was not associated with an increase of pro-inflammatory cytokines such as IFN-γ, IL-4, and TNF-α (FIG. 2D). These experiments were performed using FIX&PERM (ADG, Austria) according to the manufacturer's protocol along with the following antibodies: FITC-labelled IFN-γ (B27) and IL-4 (8D4-8) (BioLegend, Germany) and APC-labeled TNF-α (MAb 11) (BD Biosciences, Germany). These data were gathered on a FACS Calibur or LSRII flow cytometer and analyzed using CellQuest software (BD Biosciences, USA).

Example 3: GZ-αβTCR-Treatment Effects on Cells in Peripheral Blood in a Murine Model of Hu-PBL NOD-scid IL2rγ$^{null}$ mice (NOD-scid IL2 receptor gamma chain knockout mice; NSG mice; NOD.Cg-PrkdcscidIl2rgtm1Wjl/SzJ mice) are NOD-scid mice that bear a targeted mutation in the IL-2 receptor gamma chain gene and are used in a model for the study of human islet alloreactivity (the huPBL model). These mice have previously been demonstrated to allow the engraftment of huCD45+ cells at high levels with low inter- and intra-donor variability (King et al., Clin Exp Immunol 2009(157)). Three weeks after an injection of hPBMC cells, the huCD45+ cells seen in the peripheral blood were almost all (>98%) CD3+ and retained their function. Furthermore, the γδ T-cell engraftment during this time period was below 1% of the huCD45+ cells. Additionally, three weeks after the injection of hPBMCs, the percentage of huCD45+ cells in the spleen reached a plateau until day 30, which provided a timeframe of 7 days to study the effect of the αβ mAb treatment in vivo.

Figure 3A:
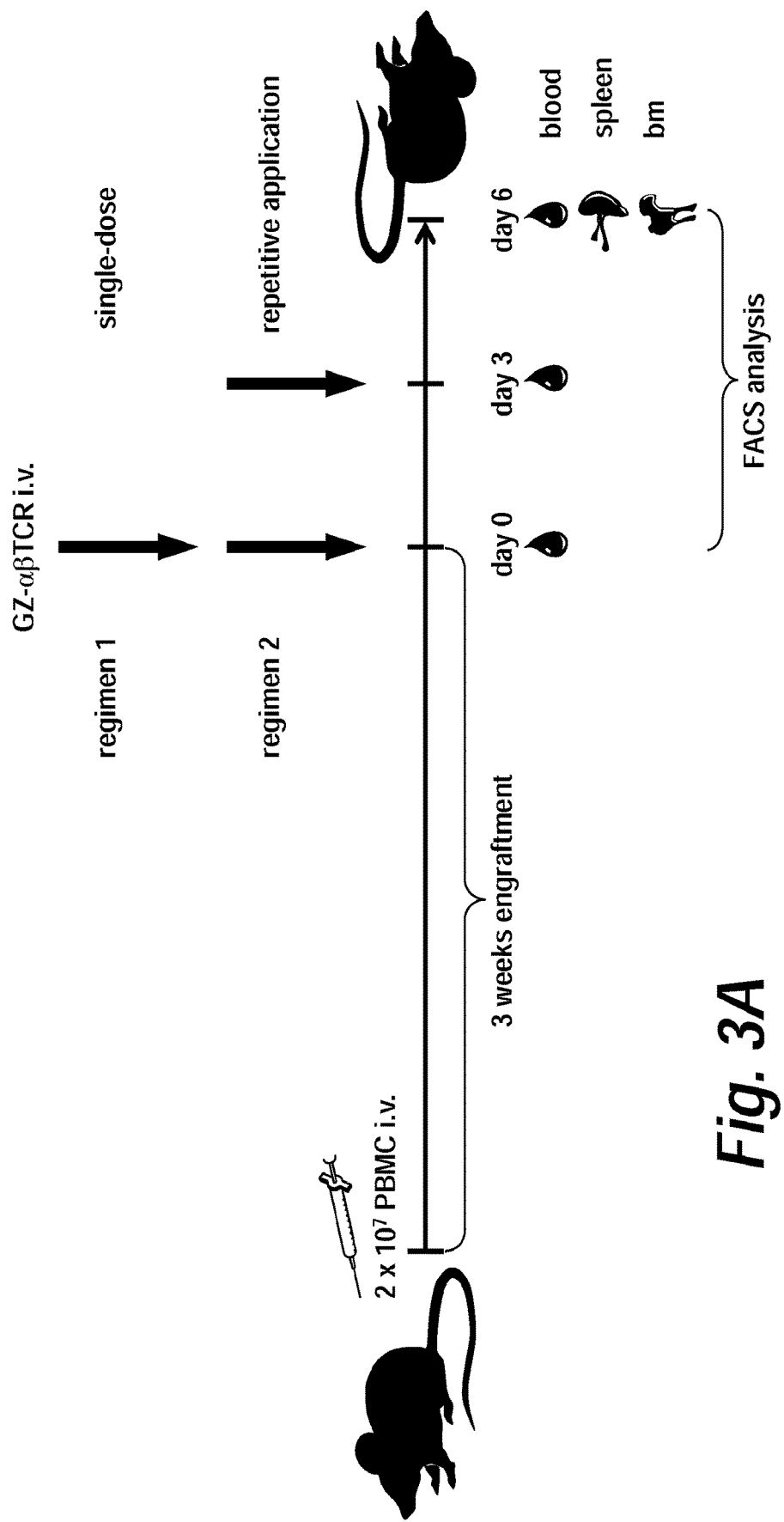
FIGS. 3A-3B depict results from a mouse model of GVHD.

NSG mice between the ages of 6 and 20 weeks old were obtained from the Jackson Laboratory (Maine, USA) and housed in single air flow cages under specific pathogen-free conditions. All experimental NSG mice received 2×10$^7$ hPBMC intravenously (through the tail vein), and the engraftment of huCD45+ cells in the peripheral blood of the mice was assessed three weeks later through FACS-staining Mice were then matched into two groups and i.v.-injected with either GZ-αβTCR (20 μg/mouse) at day 0, GZ-αβTCR (20 μg/mouse) at day 0 and 3, or PBS (100 μL) as a control (FIG. 3A).

Figure 3B:
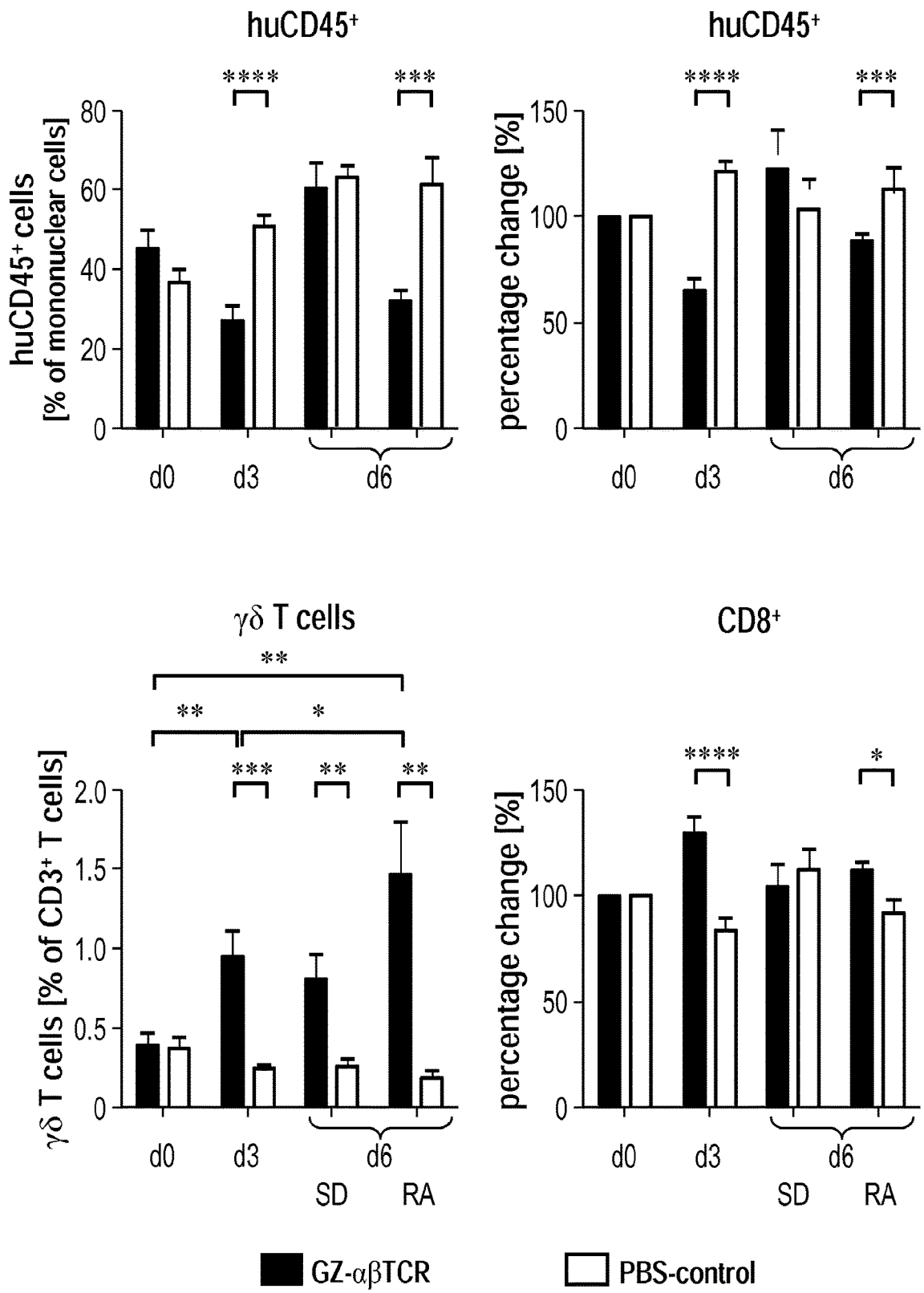

Analyses of peripheral blood were performed for human CD45+, CD4+, CD8+, and γδ T cells at day 0, 3, and 6 after a control injection, single dose (SD) or repetitive application (RA) of GZ-αβTCR (FIG. 3B). A single injection of GZ-αβTCR reduced the percentage of human hematopoietic cells in the blood significantly at day 3 (FIG. 3B, p<0.001) but this effect was no longer evident at day 6 and the engraftment in treated mice (n=9) did not differ from the engraftment in control mice (n=8; FIG. 3B). However, repetitive injections of GZ-αβTCR on both days 0 and 3 (FIG. 3A) resulted in mice with significantly lower levels of engrafted huCD45+ cells (n=9) when compared to control (PBS injected; n=9) mice on day 6 (FIG. 3B, p<0.001).

Similarly, the short-term reduction of mostly CD4+αβ T cells (FIG. 3B) after a single injection was no longer evident at day 6, whereas repetitive application of the GZ-αβTCR resulted in clear, preserved, and significant (p<0.05) decline of CD4+αβ T cells compared to PBS-treated control mice at day 6 (FIG. 3B). Accordingly, this increased the relative proportion of CD8+αβ T cells (FIG. 3B).

The percentage of CD4+ and CD8+ cells among the CD3+αβ T-cells in the peripheral blood cells was set at 100% and the histogram plots show the percentage change of human CD4+ cells (upper right) and the percentage change of human CD8+ cells (lower right) as compared to the initial value at day 0 (FIG. 3B).

Figure 4:
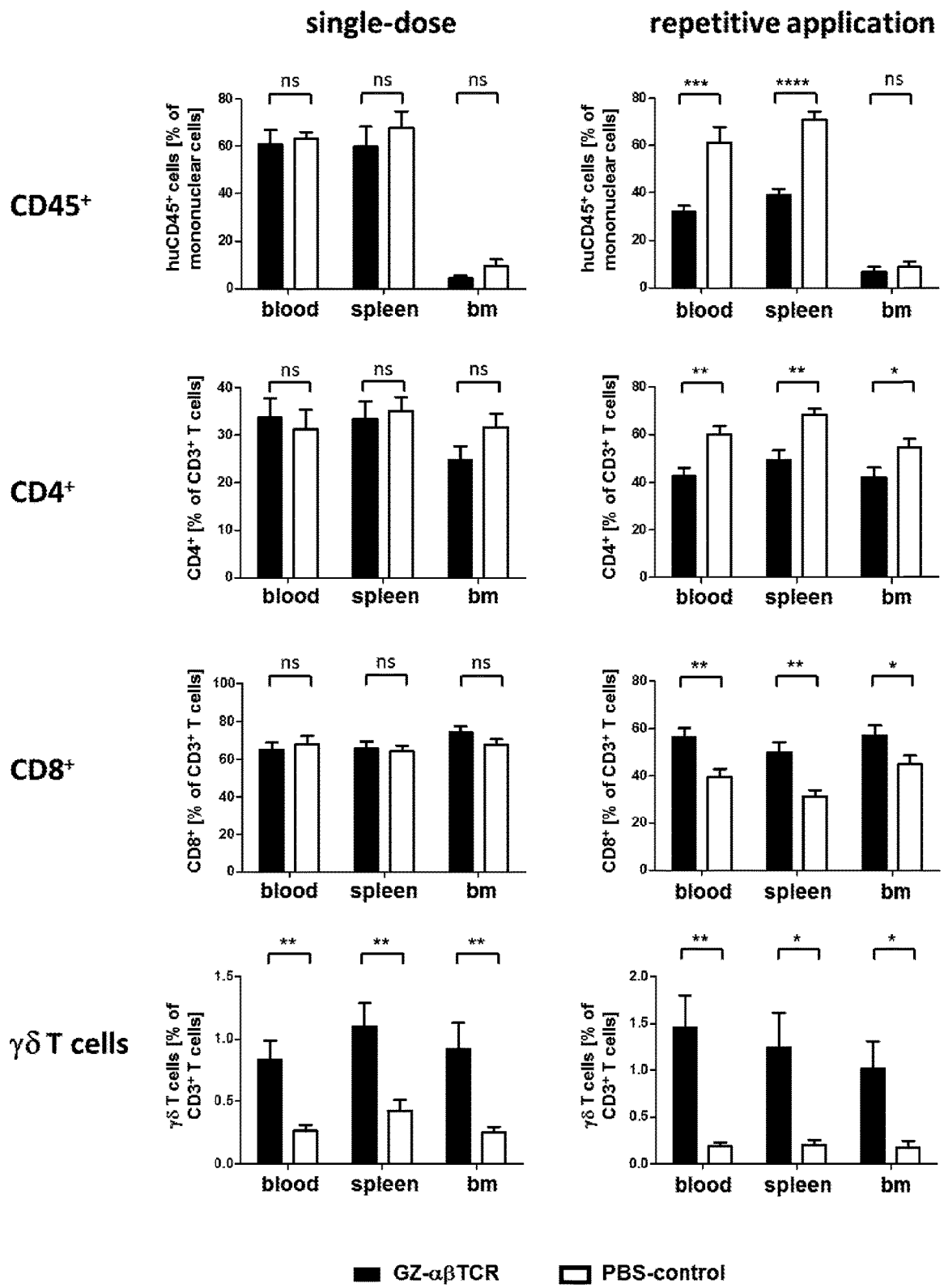
FIG. 4 is a series of histogram plots depicting the percentage of human CD45+ cells, CD4+ T cells, CD8+ T cells and γδ T cells in peripheral blood, spleen and bone marrow (bm) at day 6 after single dose (SD, left column) or repetitive application (RA, right column) of GZ-αβ TCR. Error bars present SEM; d0 and d3: ■n=18, □n=17; d6 SD: ■n=9, □n=8; d6 RA: ■n=9, □n=9. $*p<0.05$; $p<0.01$; $*p<0.001$, $****p<0.0001$.

Example 4: GZ αβTCR-Treatment Effects on Cells in Peripheral Blood, Spleen, and Bone Marrow in a Murine Model of Hu-PBL Six days after treatment using a single dose of GZ-αβTCR, the levels of engrafted huCD45+ and CD3+ T cells in peripheral blood were unchanged (Example 3). Likewise, the engraftment of huCD45+ cells in spleen and bone marrow did not deviate compared to the PBS-treated control (FIG. 4). Furthermore, no difference was seen in the CD4+/CD8+ T-cell ratio in any of the organs tested.

However, repetitive treatment (two doses) reduced the huCD45+ cell not only in peripheral blood (p<0.001), but also in the spleen (p<0.0001) compared to control mice at day 6 after treatment. Repetitive treatment did not reduce the level of huCD45+ cells in the bone marrow of these mice (FIG. 4).

Moreover, this repetitive treatment using GZ-αβTCR preferentially reduced CD4+ T cells in peripheral blood (p<0.01) and in the spleen (p<0.01) at day six (FIG. 4). Interestingly, the same effect was also observed in the bone marrow (p<0.05), where overall engraftment levels of huCD45+ cells were unaffected. Consequently, the reduction of CD4+αβ T cells resulted in a relative increase in the proportion of CD8+αβ T cells in peripheral blood (p<0.01), spleen (p<0.01), and bone marrow (p<0.05, FIG. 4).

Simultaneously to the overall decline in the proportion of CD3+ T cells and αβ T cells in huCD45+ cells, a proportional increase of γδ T cells was observed in the peripheral blood three days after a single GZ-αβTCR injection (FIG. 3B, p<0.01). The proportion of γδ T cells in GZ-αβTCR-treated mice was elevated at both day 3 (FIG. 3B, p<0.01) and at day 6 (FIG. 3B, p<0.01) compared to PBS-treated mice after a single injection. After multiple applications of αβ mAb, a further significant increase in the proportion of γδ T cells was seen from day 3 to day 6 in the peripheral blood (FIG. 3B, p<0.05).

A significant increase in the proportion of γδ T cells/CD3+ T cells was also observed in spleen and bone marrow six days after GZ-αβTCR-treatment. Thus, both the single application and multiple applications led to a significantly higher proportion of γδ T cells in the spleen (p<0.01 and p<0.05) and bone marrow (p<0.01 and p<0.05) at day 6.

Example 5: Repetitive αβ mAb Application Results in T-Cell Modulation in Hu-HSC-Model Human CD34+ stem cells were derived from a surplus of G-CSF mobilized peripheral blood stem cells from parental donors that had been T-cell reduced by CD34+ selection (CliniMACS, Miltenyi, Germany). Informed consent regarding the scientific use was obtained from all donors in accordance with the Declaration of Helsinki.

NSG mice (see above) were sub-lethally irradiated (250 cGy) using a $^{137}$Cs irradiator (Gammacell 1000 Elite; MDS Nordion, Fleurus, Belgium). Four hours later, the mice received $1 \times 10^6$ human donor derived CD34+ hematopoietic stem cells. Reconstituted mice received weekly intravenous injections of 20 µg Fc-IL-7 fusion protein per mouse generously provided by Merck (Germany). These CD34+-engrafted mice display all the hematopoietic lineages of a healthy human immune system.

Figure 5A:
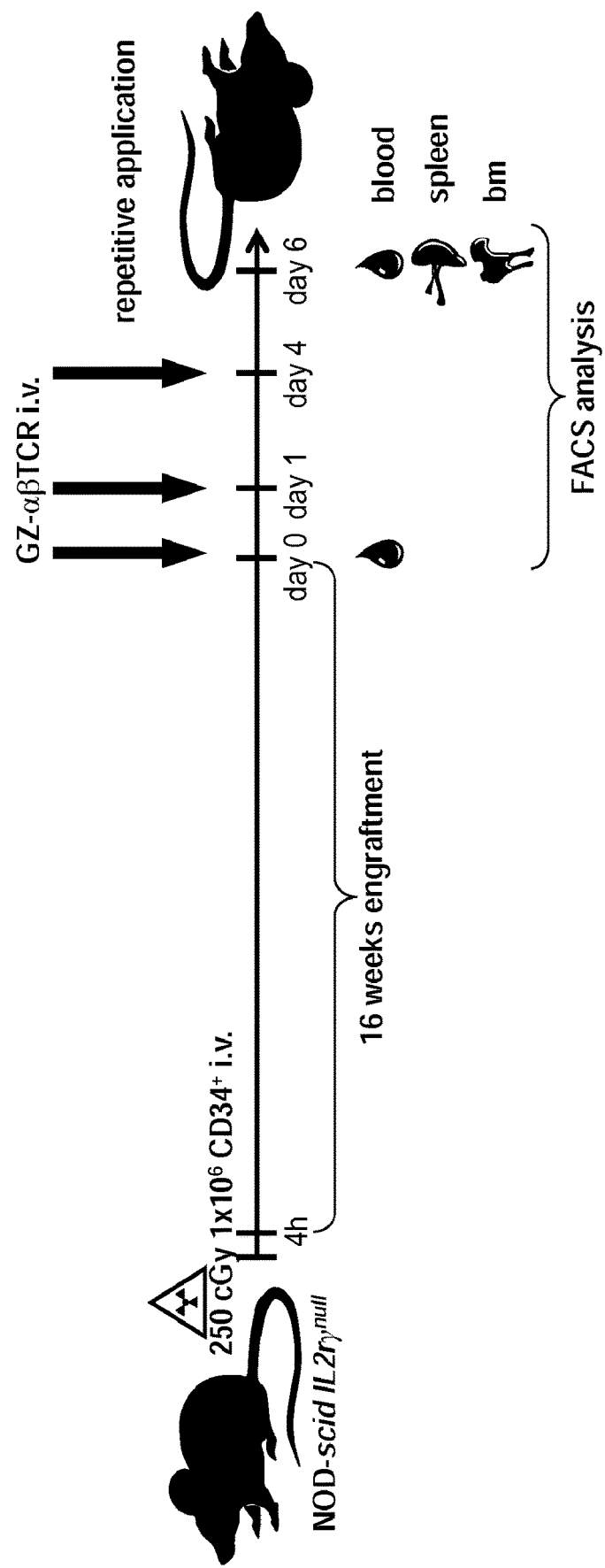
FIGS. 5A-5B graphically depict an experiment performed using the hu-HSC-NSG model.

Repetitive GZ-αβTCR-treatment (three doses, see schematic of experiment in FIG. 5A) significantly reduced CD3+ T cells in peripheral blood, spleen, and bone marrow (each p<0.05) in contrast to control mice at day 6. Moreover, the proportion of γδ T cells among CD3+ T cell significantly increased after αβ mAb treatment (blood p<0.05, spleen p<0.0001, bone marrow p<0.05, FIG. 5B).

Figure 5B:
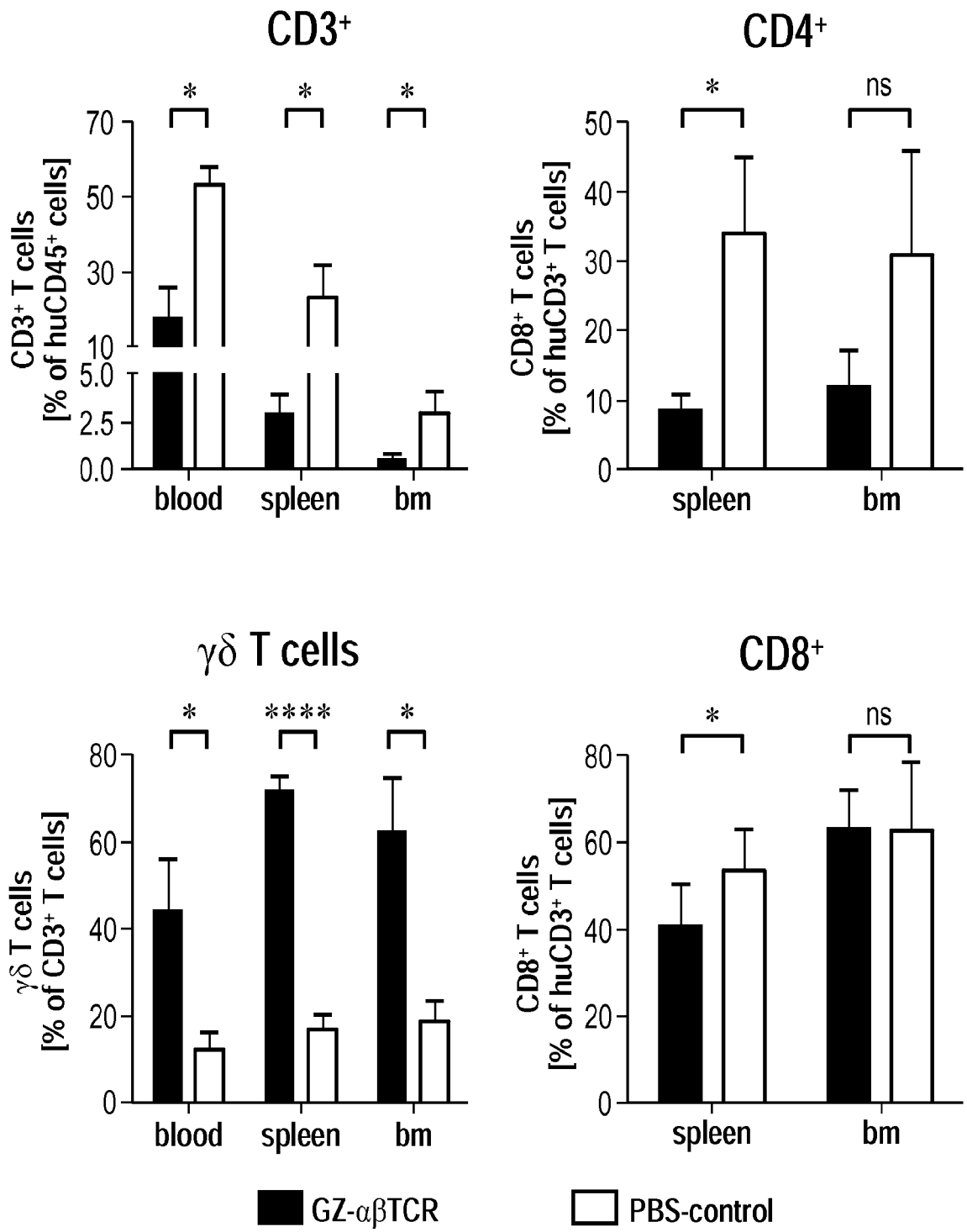

The preferential reduction of CD4+ T cells after GZ-αβTCR-treatment was significant in spleen (p<0.05) in this model, while the decline in bone marrow was not (FIG. 5B).

---

What is claimed is:

1. A method of treating a T cell-mediated disorder in a human subject in need thereof, the method comprising administering to the human subject a humanized anti-αβTCR monoclonal antibody, wherein the humanized monoclonal antibody comprises a heavy chain variable region comprising the amino acid sequence set forth in SEQ ID NO: 16, and a light chain variable region comprising the amino acid sequence set forth in SEQ ID NO: 14, wherein the T cell-mediated disorder is selected from the group consisting of a xenotransplant-related disorder, an allotransplant-related disorder, multiple sclerosis, and type 1 diabetes, and wherein the monoclonal antibody is administered intravenously to the human subject in two or more single dosage units of the humanized monoclonal antibody, and wherein the second and subsequent doses are administered to the human subject at a dosage interval of every 1, 2, or 3 days, such that the proportion of γδ T cells within a CD3+ T cell population increases in the human subject.

2. The method of claim 1, wherein three or more doses are administered.

3. The method of claim 1, wherein the T cell-mediated disorder is selected from the group consisting of a xenotransplant-related disorder and an allotransplant-related disorder.

4. The method of claim 1, wherein the administering enhances one or both of innate immunity and adaptive immunity in the human subject.

5. The method of claim 1, wherein αβ T cells are reduced relative to γδ T cells in one or any combination of peripheral blood cells, spleen, and bone marrow.

6. The method of claim 1, wherein the T cell-mediated disorder is an allotransplant-related disorder.

7. The method of claim 1, wherein the method spares pathogen inactive cells while suppressing a T cell-mediated response in the human subject.

8. The method of claim 7, wherein the pathogen inactive cells are selected from the group consisting of CD3+ effector cells, γδ T cells, iNK T cells, and NK cells.

9. The method of claim 1, wherein the method specifically eliminates alloreactive T cells in the human subject.

10. The method of claim 1, wherein the T cell-mediated disorder is selected from the group consisting of multiple sclerosis and type 1 diabetes.

11. The method of claim 1, wherein the two or more single dosage units are administered every three days.

* * * * *

UNITED STATES PATENT AND TRADEMARK OFFICE
CERTIFICATE OF CORRECTION

| | |
|---|---|
| PATENT NO. | : 11,142,575 B2 |
| APPLICATION NO. | : 15/029770 |
| DATED | : October 12, 2021 |
| INVENTOR(S) | : Blank et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 580 days.

Signed and Sealed this
Twenty-fifth Day of February, 2025

Coke Morgan Stewart
*Acting Director of the United States Patent and Trademark Office*